US006231863B1

(12) United States Patent
Colau et al.

(10) Patent No.: US 6,231,863 B1
(45) **Date of Patent: *May 15, 2001**

(54) DNA SEQUENCES, MOLECULES, VECTORS AND VACCINES FOR FELINE CALICIVIRUS DISEASE AND METHODS FOR PRODUCING AND USING SAME

(75) Inventors: Didier Colau, Grez-Doiceau; Joël Roos, Frasnes-Lez-Anvaing, both of (BG)

(73) Assignee: American Cyanamid Company, Madison, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/872,056

(22) Filed: Jun. 10, 1997

(51) Int. Cl.[7] ........................ A61K 39/125; C07H 21/02; C07K 14/08; C12N 7/01

(52) U.S. Cl. .................................. 424/186.1; 424/196.11; 424/199.1; 424/216.1; 424/229.1; 435/235.1; 435/236; 435/239; 536/23.72

(58) Field of Search ............................ 424/186.1, 196.11, 424/199.1, 216.1, 229.1; 435/471–475, 235.1, 236, 239, 69.3; 536/23.72

(56) References Cited

FOREIGN PATENT DOCUMENTS

| | | |
|---|---|---|
| WO91/01332 | 2/1991 | (WO) . |
| WO94/03621 | 2/1994 | (WO) . |
| WO 95/30000 | 11/1995 | (WO) . |

OTHER PUBLICATIONS

Yokoyama, N. et al., "Recombinant Feline Herpesvirus Type 1 Expressing Immunogenic Proteins Inducible Virus Neutralizing Antibody Against Feline Calcivirus in Cat," *Vaccine*, 14(17): 1657–63 (Dec. 1996).

Geissler, K. et al., "Genetic and Antigenic Heterogeneity Among Feline Calicivirus Isolates From Distinct Disease Manifestations," *Virus Research*, 48:193–206 (1997).

Richard C. Wardley et al., Journal of General Virology, "The use of feline herpesvirus and baculovirus as vaccine vectors for the gag and env genes of feline leukaemia virus", 1811–1818 (1992).

RF Gesteland, JF Atkins, The RNA World, "The Nature of Modern RNA Suggests a Prebiotic RNA World" (1993).

John F. Timoney et al., Hagan and Bruner's Microbiology and Infectious Diseases of Domestic Animals, Eighth Edition.

Senapathy, P. et al., Methods in Enzymology, "Splice junctions, branch point sites and exons: sequence statistics, identification and application to genome project", vol. 183, pp. 252–278.

Ed Harlow and David Lane, Antibodies A Laboratory Manual, (1988).

*Primary Examiner*—Phuong T. Bui
(74) *Attorney, Agent, or Firm*—Barbara L. Renda

(57) ABSTRACT

Nucleotide sequences obtained from the genome of the capsid gene of FCV strain 2280 wherein the splicing sites have been modified, so as to be deleted or inactivated are provided. The nucleotide sequences include DNA sequences that encode polypeptides, such as the capsid gene of FCV strain 2280, whereby the coding sequences are capable of being transcribed in the nucleus of a eukaryotic organism without the DNA coding sequence being altered by the organism's natural splicing machinery and the amino acid structure of the expressed protein is not altered. The recombinant molecules may be incorporated into FHV-1 vectors that are used to infect cell cultures for use, inter alia, in the development of vaccines and, in particular vaccines for preventing or treating FCV disease. Also provided are methods for obtaining nucleotide sequences coding for polypeptides that are naturally transcribed in the cytoplasm of cells and, in particular, DNA sequences coding for the FCV capsid protein, which sequences are modified so as to permit the transcription thereof in the nucleus of eukaryotic cells without the modified coding sequence being altered by the eukaryotic cells' splicing machinery.

45 Claims, 15 Drawing Sheets

ATGTGCTCAACCTGCGCTAACGTGCTTAAATACTATGGCTGGGATCCCCACTTTAGATTA
GTTGTCAACCCCAACAAATTCCTTTCTGTTGGCTTTTGTGATAACCCTCTTATGTGTTGC
TATCCAGACTTGCTTCCTGAATTTGGAACCCTGTGGGACTGTGACCAGTCTCCACTACAA
ATTTATTTGGAATCTATTCTTGGAGATGATGAATGGGCTTCTACCTATGAGGCCATTGAT
CCCAGCGTACCCCCAATGCACTGGGATGCTATGGGTAAGATTTTCCAACCACACCCTGGC
GTTCTGATGCACCATATCATTGGTGAAGTCGCCAAGGCTTGGGACCCAAACCTACCACTG
TTTTGCTTAGAGGCTGATGATGGTTCTATCACGGCCCCTGAGCAAGGAACGGTTGTTGGT
GGGGTCATTGCCGAGCCTAGTGCACAAATGTCAACAGCTGCTGATATGGCCACAGGGAAA
AGCGTTGACTCTGAGTGGGAGGCATTCTTTTCCTTCCACACCAGCGTCAACTGGAGTACC
ACAGAAACTCAAGGAAAGATTTTATTCAAACAATCTTTGGGACCCCTCCTAAACCCATAC
CTTGAACATCTTGCTAAGCTGTATGTTGCTTGGTCTGGATCTATTGATGTTAGGTTCTCT
ATCTCTGGTTCTGGAGTATATGGGGGAAAACTTGCTGCCATTGTCGTACCACCTGGTGTA
GACCCCGTTCAAAGTACATCAATGCTGCAATACCCTCATGTTCTCTTTGACGCTCGTCAA
GTGGAACCAGTTATCTTCTCTATTCCTGATTTAAGGAGTACTCTCTATCACCTTATATCT
GATACTGATACTACTTCCCTTGTGATTATGGTGTATAATGATCTCATTAACCCTTATGCT
AGTGATACAAACTCTTCTGGATGCATCGTTACAGTTGAAACCAAGCCGGGGCCAGATTTC
AAGTTCCACCTTCTAAAACCACCTGGATCAATGCTGACACACGGTTCAATACCTGCTGAC
CTCATCCCAAAGTCGTCCTCCCTTTGGATTGGCAATCGCTATTGGTCTGATATCACTGAA
TTTGTTGTCCGTCCCTTTGTCTTCCAAGCAAACCGACACTTTGATTTTAATCAGGAAACT
GCTGGGTGGAGCACGCCGAGATTCCGGCCAATAACTGTTACAGTTAGTGAAAGTGGTGGG
TCAAAGCTTGGGATAGGTGTTGCAACTGACTACATTGTTCCCGGTATTCCAGATGGCTGG
CCAGACACAACAATTCCTGAAAAGCTTACCCCTGCAGGTAATTATGCAATTACAACCAGC
AATAACAGTGACATTGCTACGGCTACTGAATACGACCATGCTGATGAAATCAAAAACAAC
ACAAACTTTAAAAGTATGTACATCTGTGGATCATTGCAAAGAGCTTGGGGTGACAAGAAG
ATATCTAATACTGCTTTTATCACCACAGCAGTCAAGGAAGGTAACAGCATCACACCGTCT
AACACAATTGACATGACTAAGCTTGTTGTGTACCAGGATGCTCACGTGGGCAATGATGTG
CAAACTTCCGATGTCACCCTTGCACTTCTTGGTTACACAGGAATTGGTGAACAAGCAATT
GGTTCAGATAGAGATAGAGTGGTGCGAATCAGTGTCCTACCAGAAACTGGTGCCCGTGGC
GGCAACCACCCCATCTTCTACAAAAATACAATTAAATTGGGCTATGTGATTAGGTCTATT
GATGTGTTTAACTCCCAGATCCTCCACACGTCCAGACAACTATCCCTAAATCACTACCTG
CTTCCACCTGATTCCTTTGCTGTCTATAGAATAATTGATTCTAATGGTTCATGGTTTGAC
ATTGGTATTGATAGTGATGGTTTCTCTTTTGTTGGTGTTTCTAGTTTACCCACACTGGAA
TTTCCTCTCTCTGCCTCCTACATGGGAATTCAATTGGCAAAAATCAGGCTTGCCTCAAAT
ATTAGGAGTAGTATGACAAAATTATGA:

FIG. 1

```
1            10             20             30               40
GTT AGT GAA AGT GGT GGG TCA AAG CTT GGG ATA GGT GTT GCA ACT GAC

50             60               70             80             90
TAC ATT GTT CCC GGT ATT CCA GAT GGC TGG CCA GAC ACA ACA ATT CCT

  100            110              120            130          140
GAA AAG CTT ACC CCT GCA GGT AAT TAT GCA ATT ACA ACC AGC AAT AAC

    150             160            170              180           190
AGT GAC ATT GCT ACG GCT ACT GAA TAC GAC CAT GCT GAT GAA ATC AAA

       200            210              220          230            240
AAC AAC ACA AAC TTT AAA AGT ATG TAC ATC TGT GGA TCA TTG CAA AGA

           250            260               270            280
GCT TGG GGT GAC AAG AAG ATA TCT AAT ACT GCT TTT ATC ACC ACA GCA

290            300            310            320               330
GTC AAG GAA GGT AAC AGC ATC ACA CCG TCT AAC ACA ATT GAC ATG ACT

  340               350            360            370            380
AAG CTT GTT GTG TAC CAG GAT GCT CAC GTG GGC AAT GAT GTG CAA ACT

     390            400
TCC GAT GTC ACC CTT GCA
```

FIG. 2

DNA SEQUENCES, MOLECULES, VECTORS AND VACCINES FOR FELINE CALICIVIRUS DISEASE AND METHODS FOR PRODUCING AND USING SAME

FIELD OF THE INVENTION

The present invention generally relates to the feline calicivirus (FCV) disease and, in particular, to nucleotide sequences (nucleic acids) that encode polypeptides and to methods for obtaining and using said nucleotide sequences. The nucleotide sequences may comprise modified or recombinant DNA sequences or molecules. The nucleotide sequences are capable of being transcribed in the cytoplasm of eukaryotic cells without being disadvantageously altered by the splicing machinery naturally found in such cells. The present invention further relates to live recombinant expression vectors comprising said nucleotide sequences or molecules and to cell cultures transformed or infected with such live recombinant expression vectors. The present invention also relates to vaccines comprising such recombinant expression vectors and/or nucleotide sequences or molecules and, in particular, vaccines for preventing or treating feline calicivirus disease.

BACKGROUND OF THE INVENTION

It is known that recombinant vectors, such as the feline herpes virus vector (FHV-1), may be used as a live carrier for developing vaccines against feline pathogens, e.g., feline leukemia virus, feline immunodeficiency virus, feline calicivirus, feline parvovirus, feline coronavirus and feline Chlamydia. See, for example, WO 94/0361, WO 91/01332 and Wardley, R. C., et al., J. of Gen. Virology (1992), 73, 1811–1818. However, the use of such recombinant FHV-1 vectors typically has been restricted to expressing feline leukemia (Wardley, R. C., et al., J. of Gen. Virology (1992), 73, 1811–1818) or feline infectious peritonitis disease virus antigens (PCT/EP94/02990 (WO 95/07987)). No successful attempts of using recombinant FHV-1 vectors for expressing antigenic determinants for the feline calicivirus disease has been known. While myriad influencing factors have been postulated, no one factor or set of factors has been identified as being the source of this failure.

Almost all gene sequences that encode proteins or polypeptides in eukaryotes are characterized as either coding (exon) or non-coding (intron) sequences. Introns are precisely spliced out of the initial gene transcript (pre-mRNA) before it is transported to the cytoplasm of the cell for translation. Sequences immediately bordering splice junctions are typically conserved in eukaryotic genes. Conserved junction sequences located between an exon and an intron are generally referred to as the 5' splice sites or donor sites. Sequences located at the boundary between an intron and an exon are generally referred to as the 3' splice sites, or acceptor sites. Further, short conserved sequences, referred to as branch point sequence, are typically located within the intron, usually 10 to 50 nucleotides upstream from an acceptor site. (See The RNA World, eds. R. F. Gesteland, J. F. Atkins, Cold Spring Harbor Laboratory Press (1993)).

So called consensus sequences typically represent basic sequences of nucleotides that are derived from a large set of observed similar sequences in a specific region of a nucleic acid molecule. (See Stenesh, J., Dictionary of Biochemistry and Molecular Biology, Second Ed., John Wiley & Sons (1989)). Known consensus sequences (DNA sequences) of the splicing signals include:

5' splice site or donor site: ${}^{C}_{A}$AG/GT${}^{A}_{G}$AGT

3' splice site or acceptor site: $({}^{T}_{C})_9$NCAG/G, wherein N=A or G or T or C Branch point sequence: ${}^{C}_{T}$N${}^{C}_{T}$T${}^{A}_{G}$AC (See, P. Senapathy, et al., Methods in Enzymology, Vol. 183, pp. 252–278 (1993)).

The calicivirus capsid (C) gene encodes the calicivirus capsid protein, which has been identified as an important antigen for developing vaccines for feline calicivirus disease. Although consensus DNA sequences, which are closely related to the splicing signals (donor, acceptor and branching sites) have been identified in genes coding for other eukaryotic proteins, as well as viruses that replicate in eukaryotes, no consensus DNA sequences for the calicivirus capsid (C) protein gene, including the calicivirus capsid (C) gene of FCV strain 2280, have been identified or isolated.

In nature, feline calicivirus genes are transcribed in the cytoplasm of feline calicivirus transformed or infected cells. (See, Hagan and Bruner's Microbiology and Infectious Diseases of Domestic Animals, eds. J F Timoney, J H Gillespie, F W Scott and J E Barlough, 8th edition, Comstock Publishing Ass. Cornell University Press (1988), (2nd Printing 1992)). As such, potential splicing signals, if any, are not accessible to the splicing machinery typically located in the nucleus of such infected cells. Thus, if any splicing signals exist, then they are not able to play a role in the processing of viral RNA.

On the other hand, transcription of FHV-1 genes occurs in the nucleus of infected cells and it has been observed that some of the transcribed RNAs are spliced. Further, foreign genes inserted in a recombinant FHV-1 virus (vector) are transcribed in the nucleus of the infected cells. As a consequence, the resulting RNAs are accessible to the splicing machinery of the infected cells.

Bovine respiratory syncytial virus (BRSV) is a viral pathogen whose genes are transcribed in the cytoplasm of infected cells. It has been reported that inactivation of splicing signals in the BRSV glycoprotein G gene, which normally could not be detected in bovine cells infected with a recombinant bovine herpesvirus 1 vector (BHV-1) containing the G gene, resulted in the expression of the gene in bovine cells infected by a recombinant BHV-1 virus having the mutated gene. See F. A Rijsewijk, R. C. Ruuls, K. Westerink and J. T. Van Oirschot, Department of Bovine Virology, Institute for Animal Science and Health, ID-DLO Lelystad, The Netherlands, at the $20^{th}$ International Herpesvirus Workshop, Jul. 29–Aug. 3, 1995, University of Groningen, The Netherlands. However, the findings do not indicate, among other things, (1) the identity and position of the mutated splicing sites, (2) whether such splicing sites are present in the FCV C gene, or (3) whether the inactivation of such splicing sites, if present, would permit the complete or partial expression thereof in the nucleus of cells infected therewith.

Accordingly, there remains a need for recombinant DNA sequences, DNA molecules containing such DNA sequences that code for polypeptides or proteins that are naturally transcribed in the cytoplasm of cells and methods for making or using same. In particular, there remains a need for modified DNA sequences coding for the FCV capsid protein that are capable of being transcribed in the nucleus of eukaryotic cells without being altered by the cells' splicing machinery. Moreover, there remains a need for recombinant expression vectors that include such DNA sequences, cell cultures transformed or infected with such recombinant vectors and vaccines including such recombinant vectors and/or recombinant DNA sequences for the prevention and treatment of FCV disease.

SUMMARY OF THE INVENTION

A primary object of the present invention is to provide (1) an isolated or purified recombinant DNA sequence or molecule that is capable of being transcribed by eukaryotic cells without being disadvantageously altered by the splicing machinery of the eukaryotic cells, and (2) methods for making and using the isolated or purified DNA sequence or molecule.

Another object of the present invention is to provide recombinant or DNA sequences that code for polypeptides (proteins) that may be naturally transcribed in the cytoplasm of cells, which DNA sequences are modified so as to be capable of being transcribed in the nucleus of eukaryotic cells without being altered by the splicing machinery of the cells and without causing amino acid sequence or functional properties of the polypeptides thereof to be disadvantageously altered.

Still yet another object of the present invention to provide methods for obtaining isolated or purified recombinant DNA sequences that effectively encode the feline calicivirus (FCV) capsid protein.

A further object of the present invention is to identify or isolate DNA sequences in the feline calicivirus C gene, and in particular the FCV C gene of FCV strain 2280, that are identical or closely related to the consensus splicing sequences, signals, or sites (donor, acceptor and branching sites) and to identify or isolate DNA sequences therein that will result in either retaining, eliminating or inactivating the consensus and/or splicing sequences, signals or sites when such consensus and/or splicing sequences are modified and/or eliminated therefrom.

A further object of the present invention is to provide recombinant or modified DNA sequences or DNA molecules containing such recombinant or modified DNA sequences that are capable of encoding or expressing the FCV capsid protein without being altered by the splicing machinery of the eukaryotic cells.

It is a further object of the present invention to provide recombinces that are capable of being introduced into a eukaryotic organism through the use of live recombinant carriers (LRCs) whose transcription occurs in the nucleus of eukaryotic cells.

Another object of the present invention is to provide a live recombinant FHV-1 expression vector comprising modified or recombinant DNA sequences derived from the FCV gene that codes for the FCV capsid protein, wherein said sequences are capable of being (1) transcribed in the nucleus of eukaryotic cells without being altered by the splicing machinery of eukaryotic organisms and (2) introduced into a eukaryotic organism through the use of live recombinant carriers (LRCs) whose transcription occurs in the nucleus of eukaryotic cells.

It is a particular object of the present invention to provide DNA sequences or molecules that may be used in conjunction with an FHV-1 vector as a live carrier for the development of vaccines, including vaccines comprising antigenic determinants associated with FCV disease.

Another object of the present invention is to provide a vaccine, and in particular a vaccine for the prevention or treatment of feline calicivirus (FCV) disease, which comprises recombinant vectors and/or said recombinant DNA molecules.

A further object of the present invention, is to provide a culture of host cells that is transformed or infected a recombinant expression vector comprising modified or recombinant DNA sequences, in particular modified or recombinant DNA sequences derived from the FCV gene that codes for the FCV capsid protein, wherein said sequences are capable of being transcribed in the nucleus of eukaryotic cells without being altered by the splicing machinery the host cells.

Additional objects and advantages of the present invention will be set forth in the following detailed description or may be learned from practicing or using the present invention. The objects and advantages may be realized and attained by means of the instrumentalities and combinations particularly pointed out in the appended claims. It is to be understood that the foregoing general description and the following detailed description are exemplary and explanatory only and are not to be viewed as being restrictive of the invention, as claimed.

BRIEF DESCRIPTION OF THE DRAWINGS

The accompanying drawings, which are incorporated in, and constitute a part of the specification, illustrate embodiments of the present invention and, together with the description, serve to explain the principles of the present invention.

FIG. 1 is the nucleotide sequence of the calicivirus capsid gene of the feline calicivirus strain FCV 2280 (SEQ ID: 23).

FIG. 2 is nucleotides 1183 to 1584 (SEQ ID NO: 24) of the nucleotide sequence coding for feline calicivirus capsid gene of the feline calicivirus strain FCV 2280 of FIG. 1.

DESCRIPTION OF PREFERRED EMBODIMENTS

Figure 3:
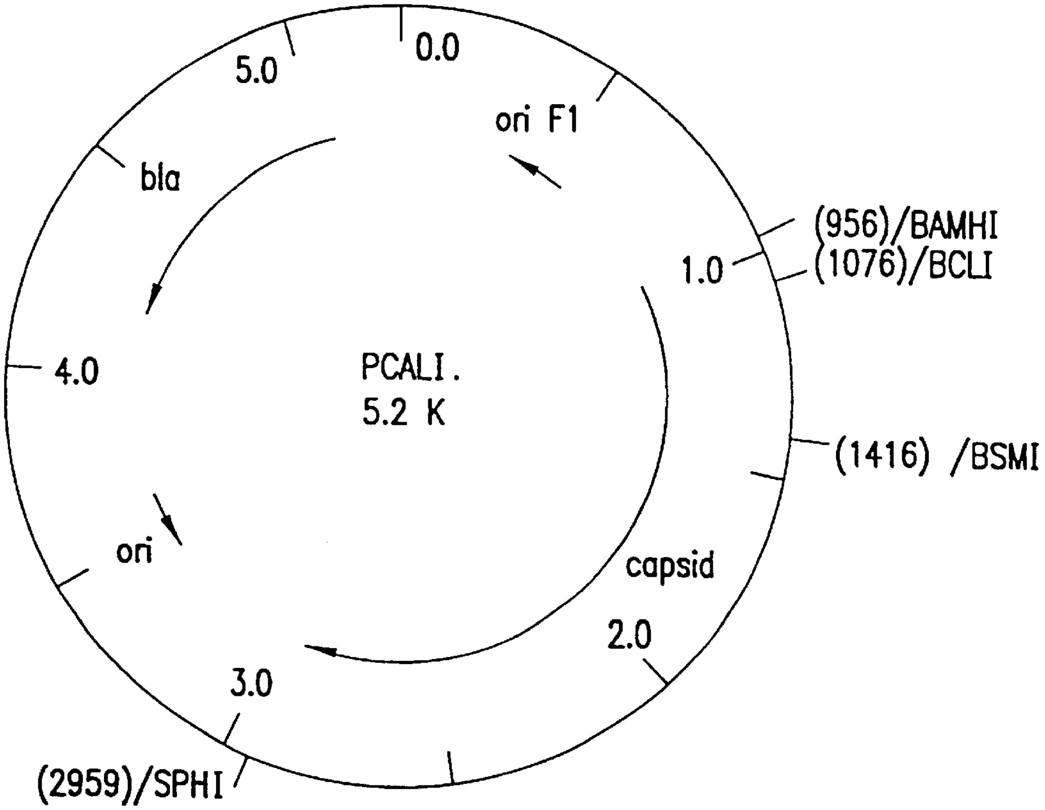
FIG. 3 represents the restriction map of plasmid pCALI.
Figure 4:
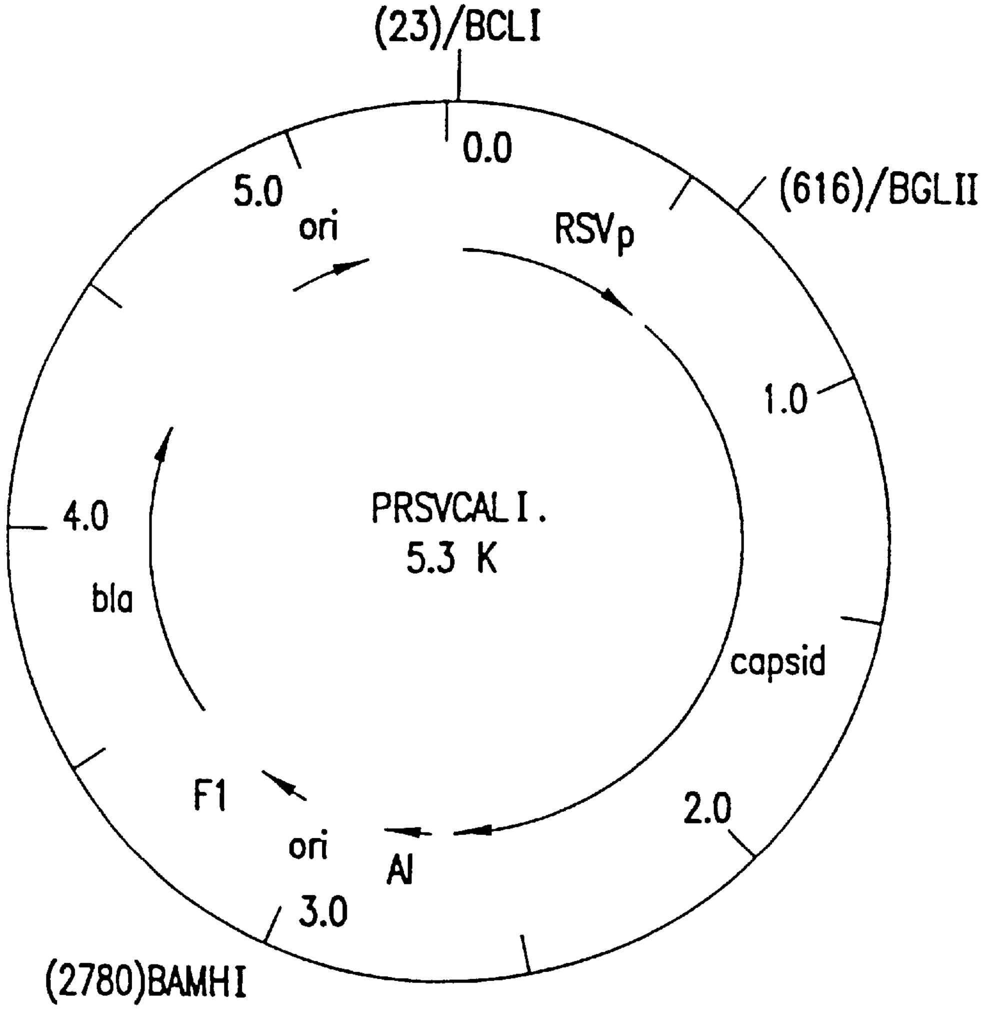
FIG. 4 represents the restriction map of plasmid pRSV-CALI.
Figure 5:
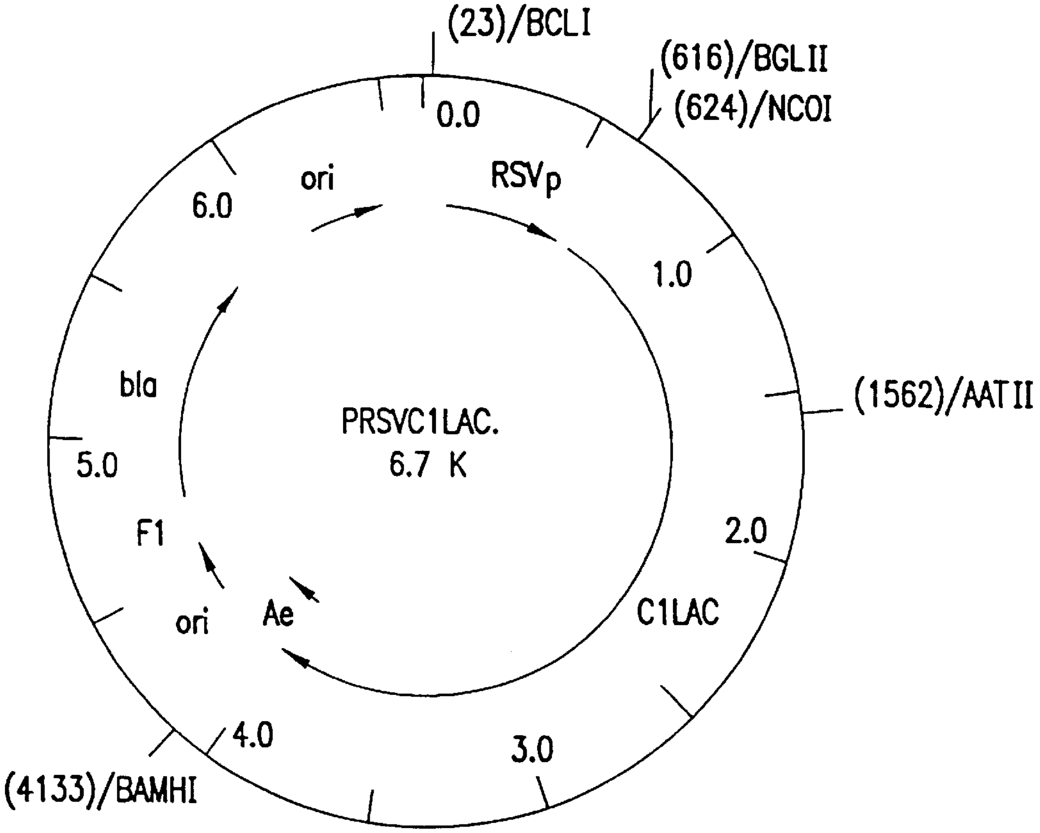
FIG. 5 represents the restriction map of plasmid pRSVC1LAC.
Figure 6:
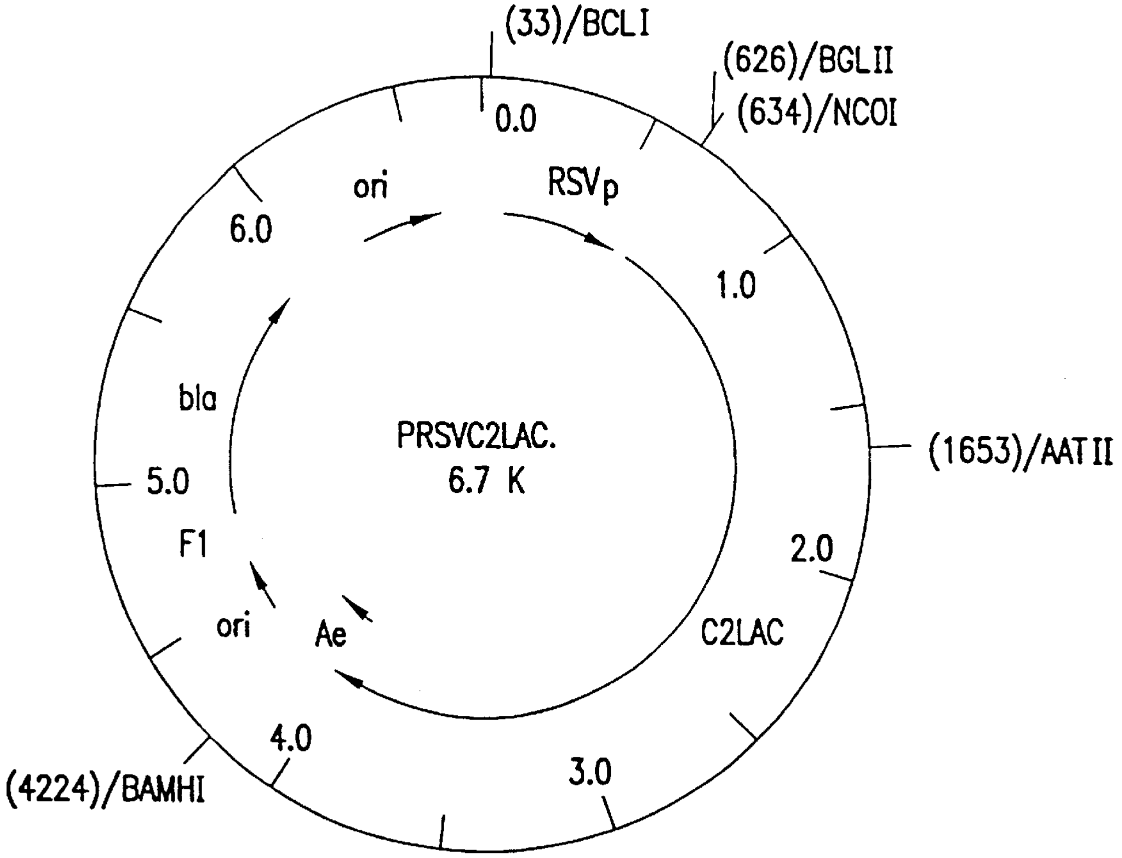
FIG. 6 represents the restriction map of plasmid pRSVC2LAC.
Figure 7:
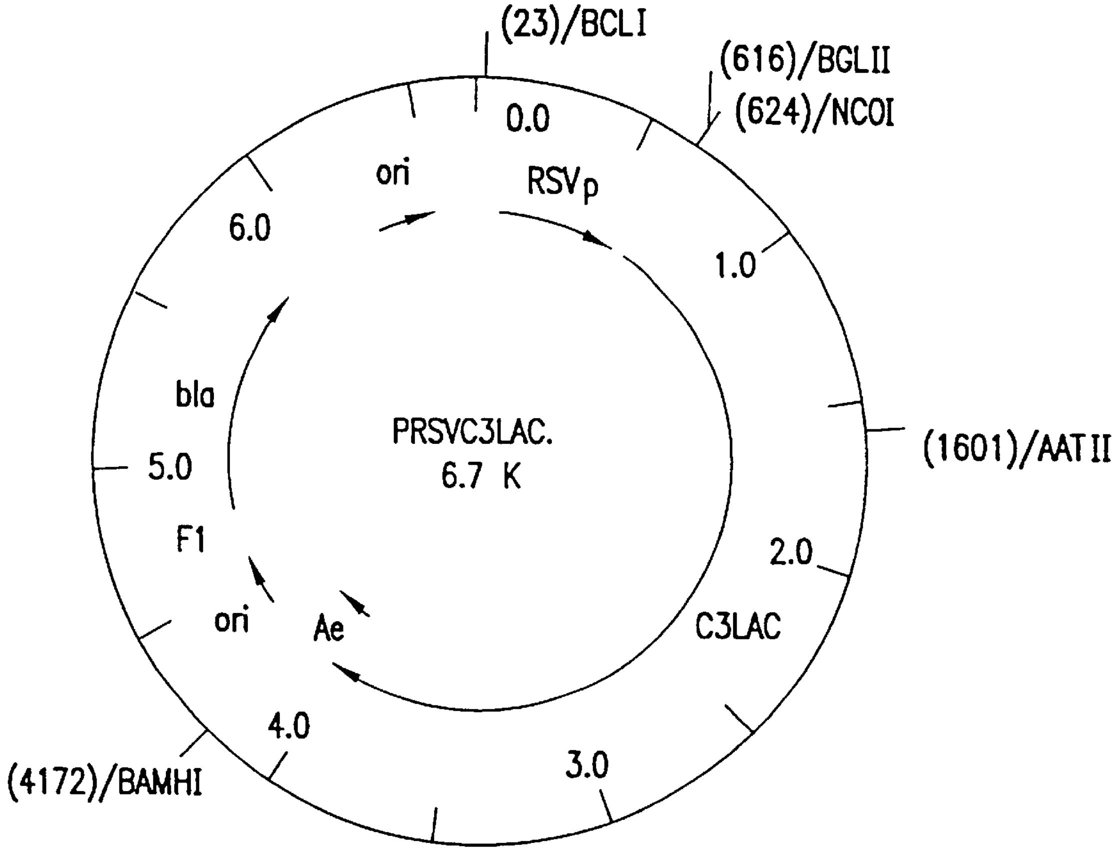
FIG. 7 represents the restriction map of plasmid pRSVC3LAC.
Figure 8:
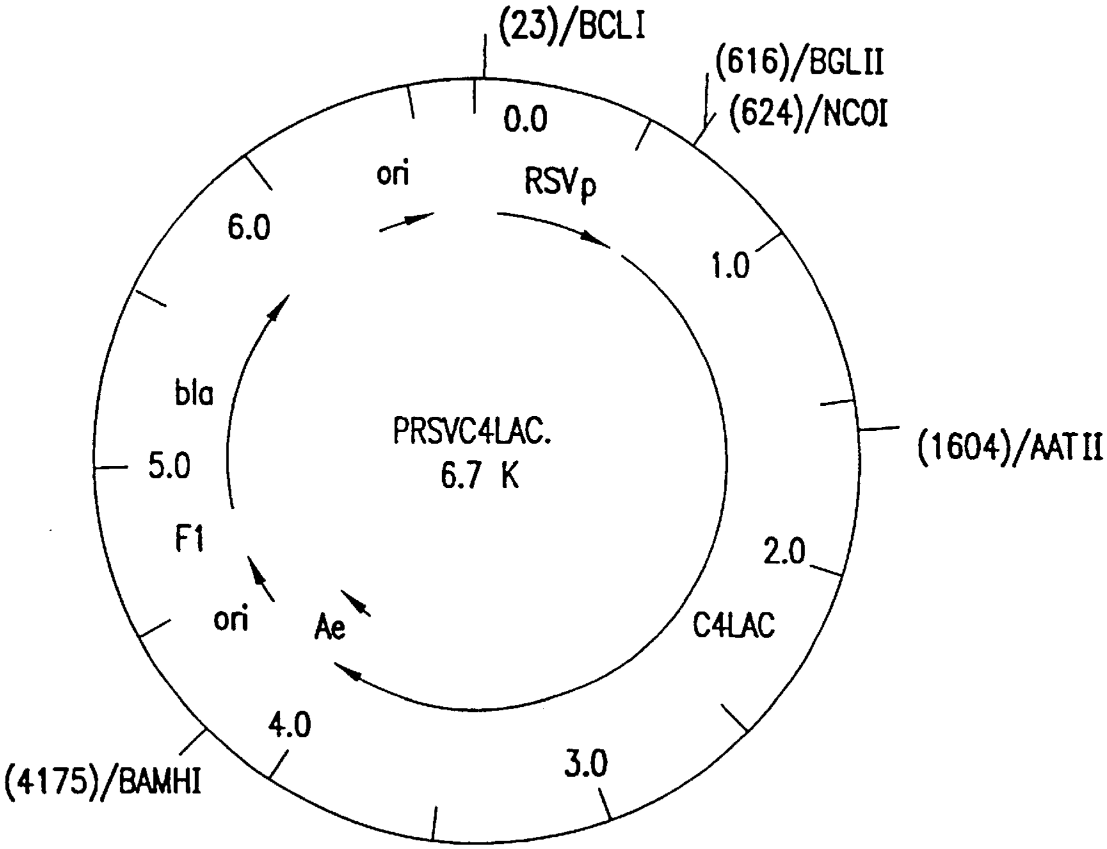
FIG. 8 represents the restriction map of plasmid pRSVC4LAC.
Figure 9:
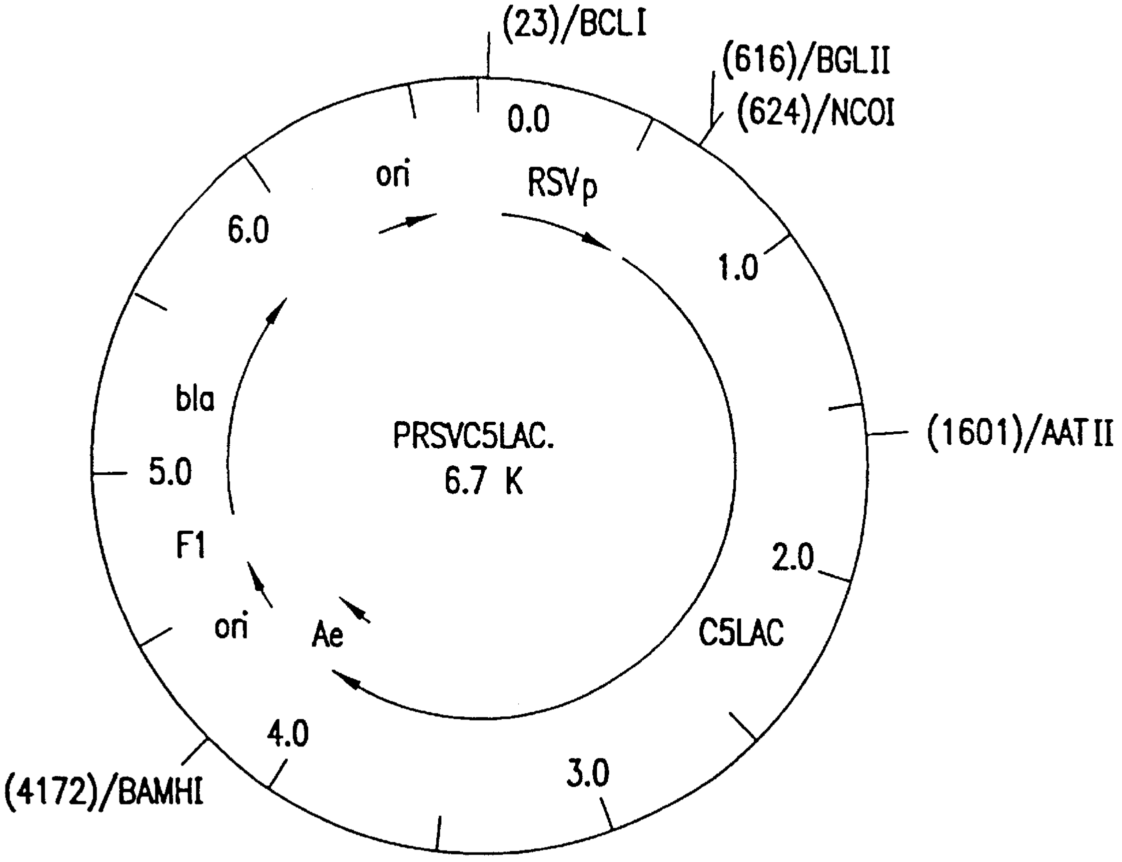
FIG. 9 represents the restriction map of plasmid pRSVC5LAC.
Figure 10:
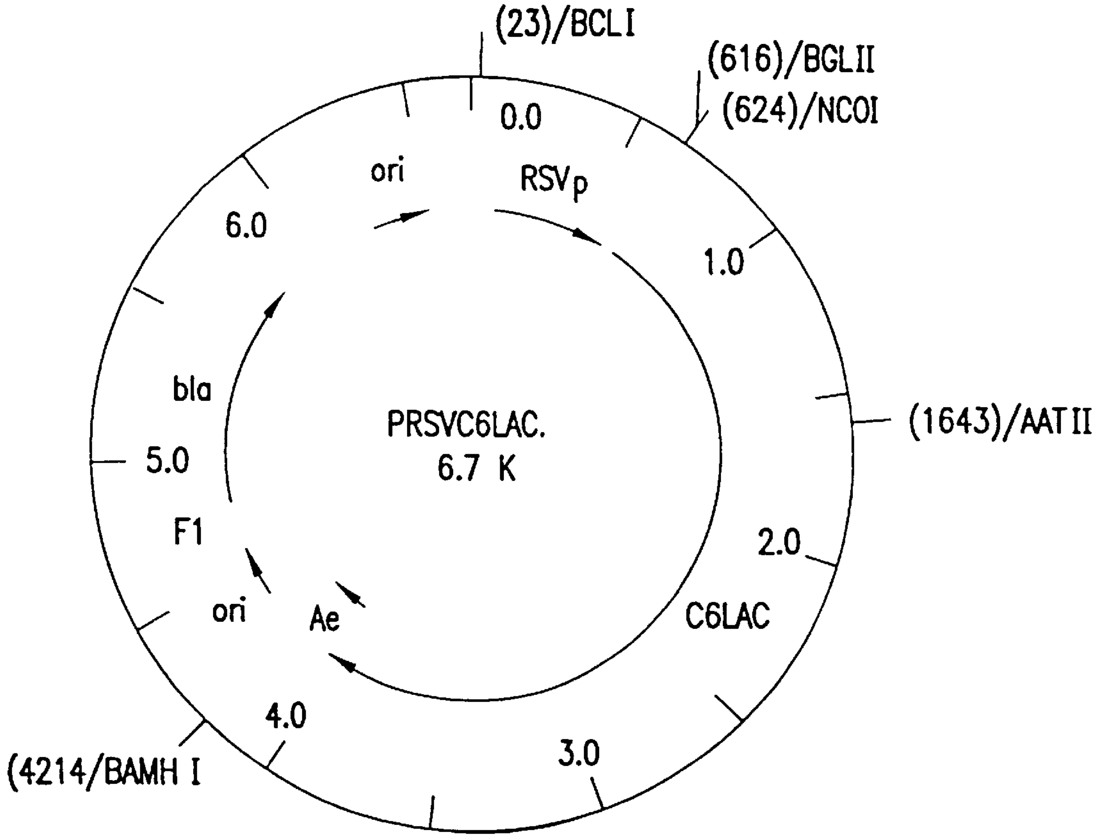
FIG. 10 represents the restriction map of plasmid pRSVC6LAC.
Figure 11:
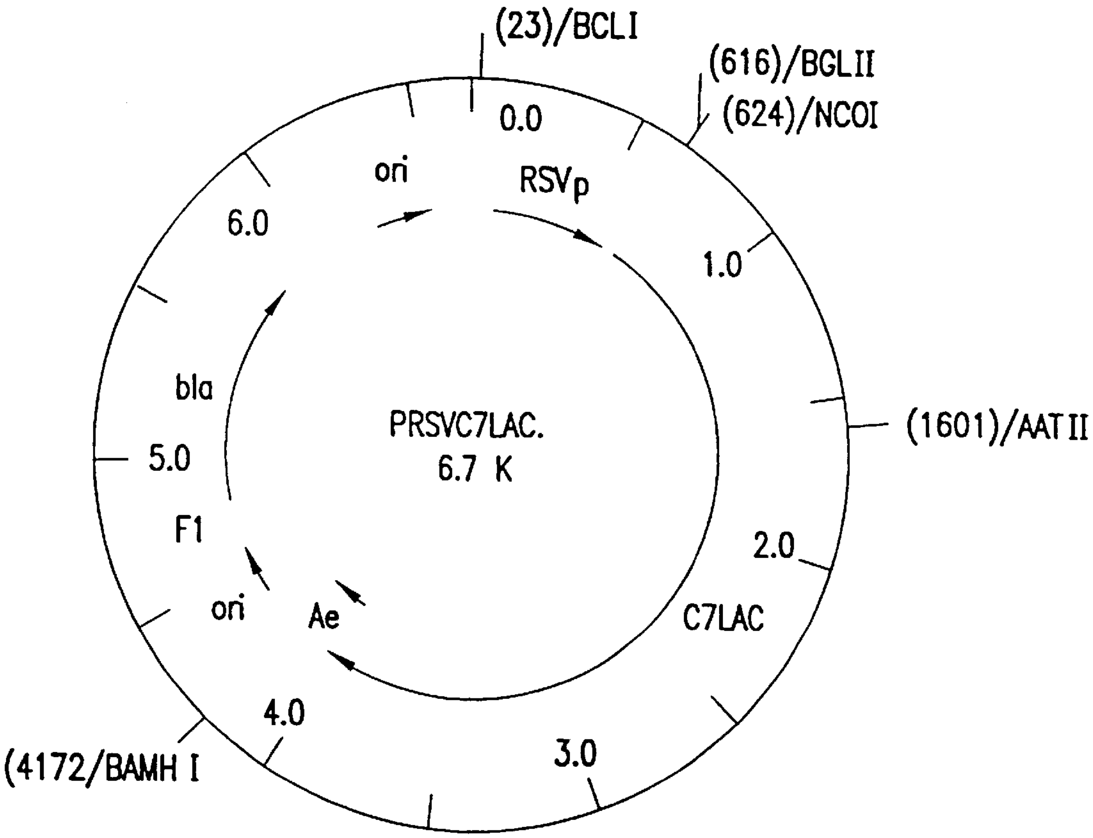
FIG. 11 represents the restriction map of plasmid pRSVC7LAC.
Figure 12:
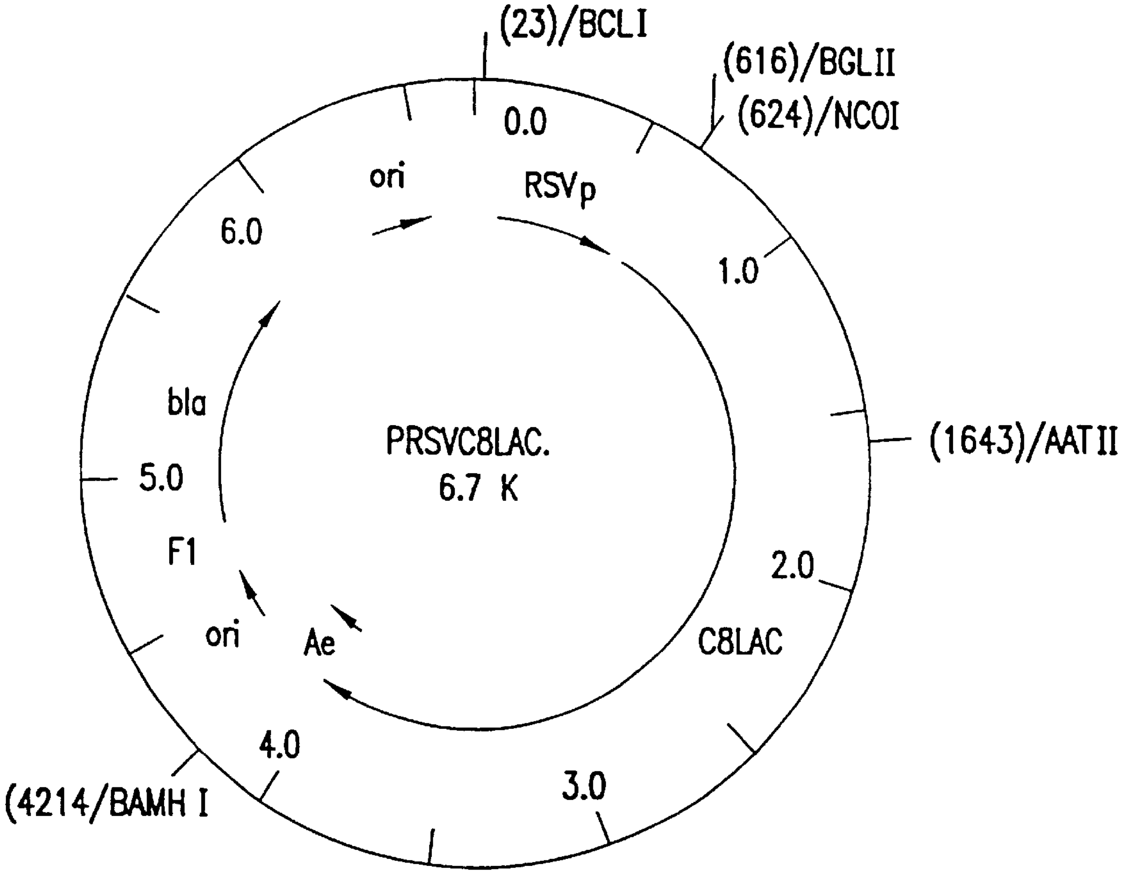
FIG. 12 represents the restriction map of plasmid pRSVC8LAC.
Figure 13:
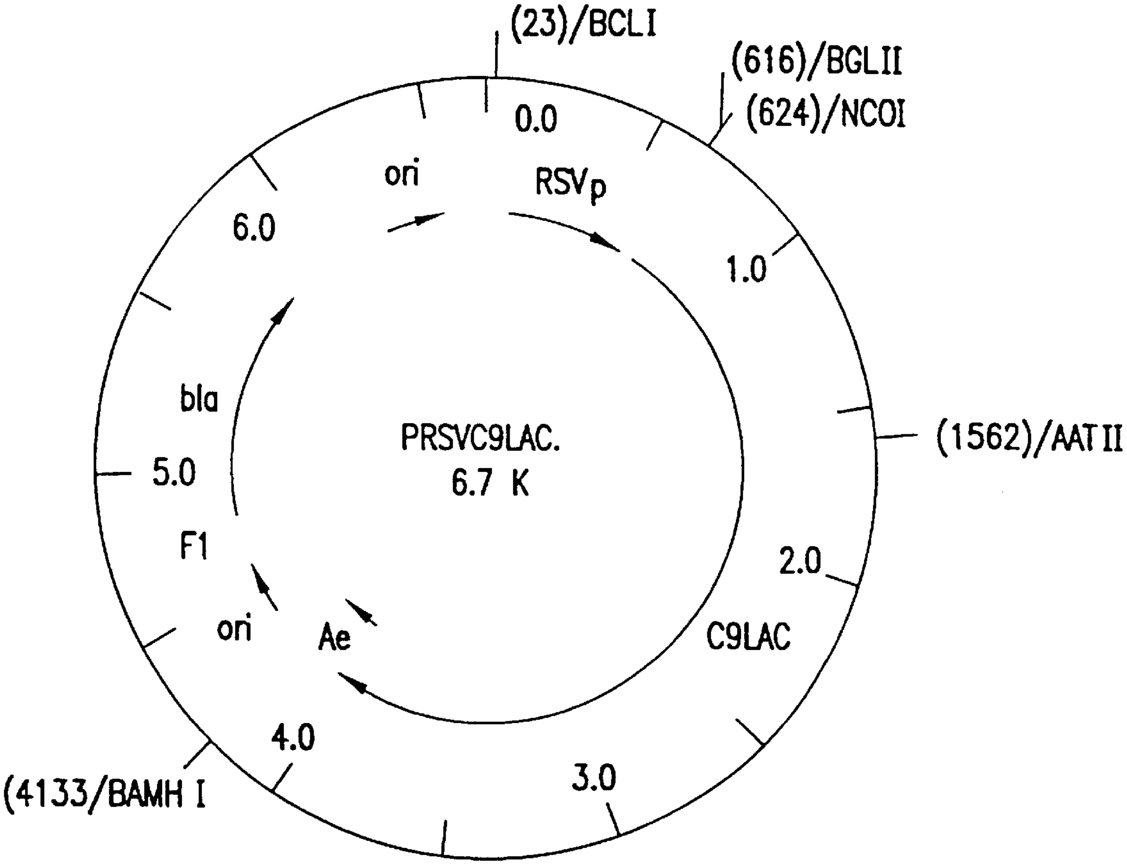
FIG. 13 represents the restriction map of plasmid pRSVC9LAC.
Figure 14:
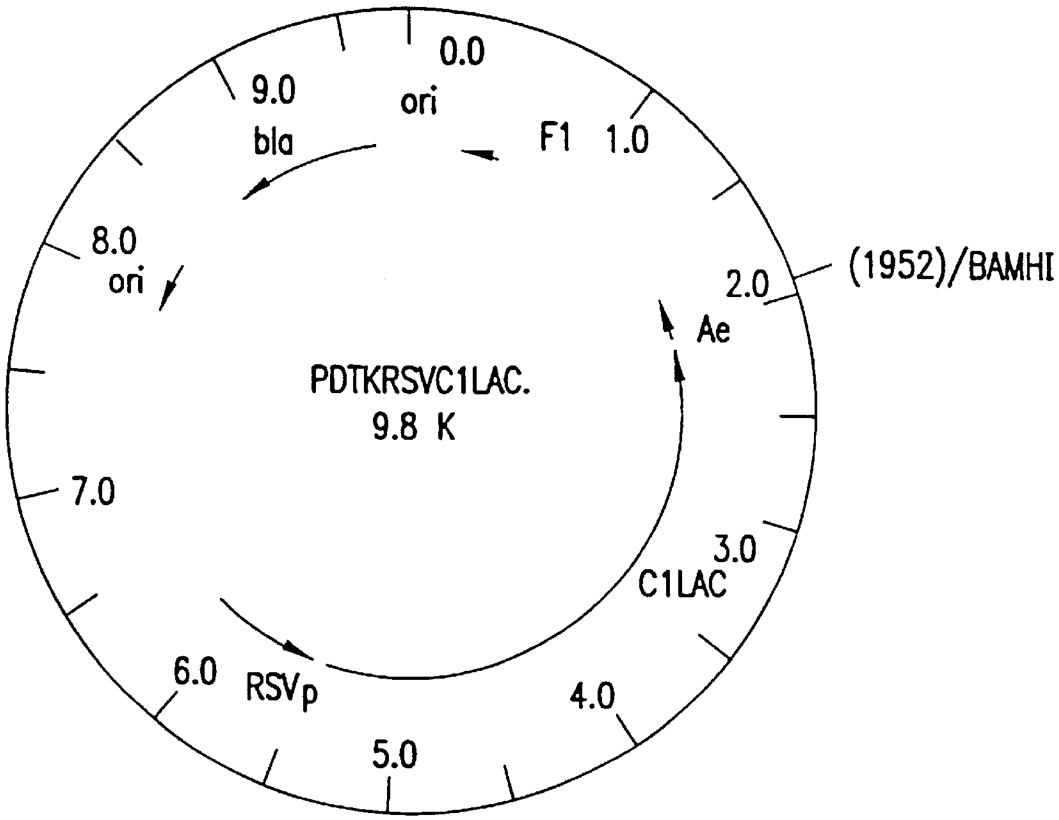
FIG. 14 represents the restriction map of plasmid pdTKRSVC1LAC.
Figure 15:
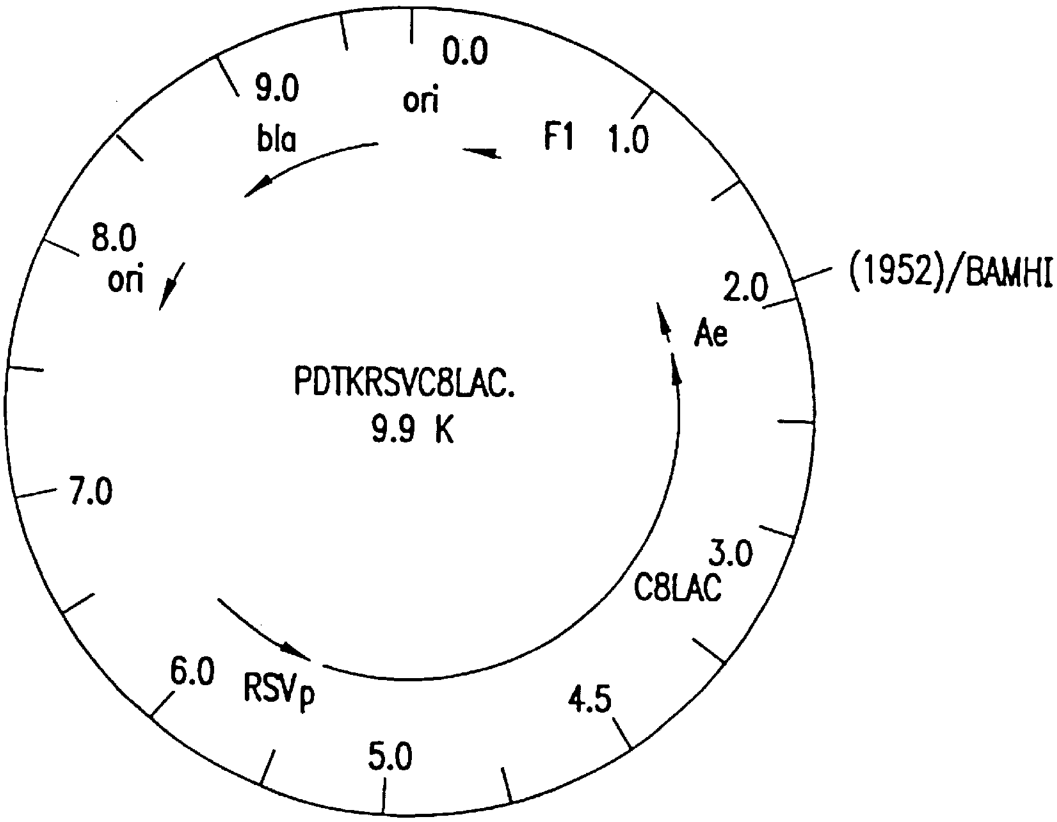
FIG. 15 represents the restriction map of plasmid pdTKRSVC8LAC.

All patents, patent applications and literatures cited in this description are incorporated herein by reference in their entirety. In the case of inconsistencies, the present disclosure, including definitions, will prevail.

Throughout this description, a feline calicivirus cell line, designated as FCV 2280, is described. For the purposes of the present invention, and to aid the skilled artisan in practicing the present invention, a cell culture, which is equivalent to FCV 2280 and designated herein as SAH-2280 MS, has been deposited with the American Type Culture Collection depository in Rockville, Md., in accordance with the Budapest Treaty. The deposited culture has been assigned ATCC Registration No. VR-2555. The depository has been instructed to afford permanence of the deposit for at least thirty years or at least five years after the most recent request, whichever period is longer. Should the deposit become non-viable or be inadvertently destroyed, the culture will be replaced (1) for at least thirty years from the date of the original deposit or at least five years from the date of the most recent request for release of a sample or (2) for the life of any patent issued on this application, whichever period is longer. With respect to the availability of the culture, the aforementioned deposit has been made under conditions that assure ready accessibility to the culture by the public when a patent is granted on this patent application, whereby all restrictions to the availability to the public of the deposited culture will be irrevocably removed upon issuance of the patent. Access to the deposit will be made available during the pendency of this patent application to one determined by the Commissioner of Patent and Trademarks to be entitled thereto.

The present invention is based, in part, on the discovery that the failure of certain DNA sequences coding for polypeptides to be expressed in the nucleus of eukaryotic host cells when introduced therein by a recombinant FHV-1 vector is due to aberrant splicing of certain nucleotide sequences that are identical or similar to consensus nucleotide splicing sites. The aberrant splicing is caused by the natural splicing machinery found in eukaryotic cells. For example, when using calicivirus capsid/LacZ fusion genes inserted in FHV-1 vectors and the like, failure of expression of such genes has been attributed to the presence of splicing signals in such foreign genes that are recognized by feline cells infected by FHV-1 expression vectors.

In accordance with the present invention, such aberrant splicing may be reduced and/or completely avoided by deleting, modifying and/or otherwise inactivating certain consensus sequences/splicing sites that may exist in DNA sequences, such as the feline calicivirus C gene, so that such consensus sequences/splicing sites are either not present or not recognized by the splicing machinery found in eukaryotic cells.

In a preferred embodiment, the present invention comprises recombinant (modified) DNA sequences that permit the transcription thereof in the nucleus of eukaryotic cells without being altered by the cells' splicing machinery. In one aspect, the present invention comprises recombinant DNA sequences of the feline calicivirus C gene, which codes for the FCV capsid protein and which contains splicing sites that have been modified or removed therefrom.

Preferably, the DNA sequences of the present invention are obtained or derived from feline calicivirus (FCV) strain 2280 in which modifications have been made in the capsid gene thereof. The preferred DNA sequences are substantially identical to that of the naturally occurring capsid gene with the exception that various of the splicing sites therein have been modified (by deletion or alteration/mutation) so that donor and/or acceptor sites are inactivated. The DNA sequences of the present invention are capable of being transcribed in the nucleus of eukaryotic organisms without being altered by the cells' splicing machinery and without functionally altering the amino acid sequence of the FCV capsid protein encoded thereby.

The preferred DNA sequences from the feline calicivirus C gene that are identical or homologous to the consensus splicing signals or sites (donor, acceptor and branching) are described below. The location and composition of these splicing sites are described below in Tables 1 and 2.

In another preferred embodiment, the present invention further comprises recombinant DNA sequences of a highly variable region of the FCV gene of FCV strain 2280 that codes for the FCV capsid protein. To identify and provide the sequences of the present invention, portions of the variable region of the C gene of FCV may be modified (by deletion or alteration/mutation) and isolated using known genetic engineering techniques. It is important to note that, in accordance with the present invention, antigenic determinants for FCV disease are located within the variable region of the capsid protein and that, since the nucleotide sequence of this region of the capsid gene is highly variable among feline calicivirus strains, the splicing signals identified herein in strain FCV 2280 can differ in sequence and position (sometimes greatly) from those found in the same region of other strains. Moreover, this region contains B-cell epitope(s) which induce sero-neutralizing antibodies in cats.

Preferred nucleotide sequences of the present invention and their position in the variable region of the capsid protein of the calicivirus C (capsid) gene of feline calicivirus strain FCV 2280 are listed below in Table 1 of the Examples. The listed sequences are closely related to the known consensus DNA sequences of the splicing signals.

The portions of the genome of FCV which are modified include portions of the variable region of the capsid gene which are either identical or closely related to the consensus sequences of the splicing signals (sites). To achieve such modification, the entire calicivirus capsid gene was cloned and sequenced, a comparison thereof with the known consensus sequences for splicing signals (donor, acceptor and branching sites) was made and those sequences within this region of the capsid gene which were identical and closely related to the known consensus sequences for splicing sites were identified.

To aid in understanding and practicing the present invention, the sequence of the cloned FCV 2280 capsid gene is presented in FIG. 1 (SEQ ID NO: 23), while the variable region of the capsid gene is presented in FIG. 2 (SEQ ID NO: 24). The precise location and composition of the splicing sites can be determined by reference to Tables 1 and 2 and FIGS. 1 and 2 below.

In particular, splicing site D1 comprises nucleotides 1–6 of the variable region of the C gene of FCV strain 2280 (nucleotides 1183–1188 of the C gene of FCV strain 2280).

Splicing site D2 comprises nucleotides 8–13 of the variable region of the C gene of FCV strain 2280 (nucleotides 1190–1195 of the C gene of FCV strain 2280).

Splicing site D3 comprises nucleotides 13–19 of the variable region of the C gene of FCV strain 2280 (nucleotides 1195–1201 of the C gene of FCV strain 2280).

Splicing site D4 comprises nucleotides 33–37 of the variable region of the C gene of FCV strain 2280 (nucleotides 1215–1219 of the C gene of FCV strain 2280).

Splicing site D5 comprises nucleotides 113–121 of the variable region of the C gene of FCV strain 2280 (nucleotides 1295–1303 of the C gene of FCV strain 2280).

Splicing site D6 comprises nucleotides 209–217 of the variable region of the C gene of FCV strain 2280 (nucleotides 1391–1399 of the C gene of FCV strain 2280).

Splicing site D7 comprises nucleotides 247–251 of the variable region of the C gene of FCV strain 2280 (nucleotides 1429–1433 of the C gene of FCV strain 2280).

Splicing site D8 comprises nucleotides 296–302 of the variable region of the C gene of FCV strain 2280 (nucleotides 1478–1484 of the C gene of FCV strain 2280).

Splicing site D9 comprises nucleotides 361–368 of the variable region of the C gene of FCV strain 2280 (nucleotides 1543–1550 of the C gene of FCV strain 2280).

Splicing site A1 comprises nucleotides 58–70 of the variable region of the C gene of FCV strain 2280 (nucleotides 1240–1252 of the C gene of FCV strain 2280).

Splicing site A2 comprises nucleotides 103–116 of the variable region of the C gene of FCV strain 2280 (nucleotides 1285–1298 of the C gene of FCV strain 2280).

Splicing site A3 comprises nucleotides 272–285 of the variable region of the C gene of FCV strain 2280 (nucleotides 1454–1467 of the C gene of FCV strain 2280).

Splicing site A4 comprises nucleotides 341–355 of the variable region of the C gene of FCV strain 2280 (nucleotides 1523–1537 of the C gene of FCV strain 2280).

The nucleotide (DNA) sequences of the present invention are designated below as C1, C3, C4, C5, C6, C7, C8 and C9. The precise characteristics of the nucleotide sequences are described below in Tables 1 and 2. Preferably, the nucleotide sequences are derived or obtained from the capsid protein gene of strain FCV 2280. Of preference among the nucleotide sequences of the present invention are sequences C1, C5, C6, C7, C8 and C9, of which C5, C7 and C9 are more preferred, C7 and C9 are even more preferred, and C7 is most preferred.

Sequence C1 is the nucleotide sequence of the capsid gene of strain FCV 2280 wherein splicing sites D1, D2, D3, D4 and D9 have been deleted therefrom.

Sequence C3 is the nucleotide sequence of the capsid gene of strain FCV 2280 wherein splicing site D9 has been deleted therefrom.

Sequence C4 is the nucleotide sequence of the capsid gene of strain FCV 2280 wherein splicing sites D1, D2, D3 and D4 have been deleted therefrom.

Sequence C5 is the nucleotide sequence of the capsid gene of strain FCV 2280 wherein splicing site D9 has been deleted therefrom and the splicing sites D4, D5 and A2 have been modified so as to be inactivated.

Sequence C6 is the nucleotide sequence of the capsid gene of strain FCV 2280 wherein splicing sites D4, D5 and A2 have been modified so as to be inactivated.

Sequence C7 is the nucleotide sequence of the capsid gene of strain FCV 2280 wherein splicing site D9 has been deleted therefrom and the splicing sites D2, D3, D4, D5 and A2 have been modified so as to be inactivated.

Sequence C8 is the nucleotide sequence of the capsid gene of strain FCV 2280 wherein the splicing sites designated herein as D2, D3, D4, D5 and A2 have been modified so as to be inactivated.

Sequence C9 is the nucleotide sequence of the capsid gene wherein the splicing sites D1, D2, D3, D4 and D9 has been deleted therefrom and the splicing sites D5 and A2 have been modified so as to be inactivated.

In another preferred embodiment, the present invention comprises DNA molecules that contain recombinant (modified) DNA sequences that are capable of being transcribed in the nucleus of eukaryotic cells without being altered by the cells' splicing machinery. The recombinant DNA molecules disclosed herein are capable of expressing the portions (antigenic determinants) of the FCV capsid protein, which is coded for thereby. In accordance with this aspect of the present invention, the recombinant (modified) DNA molecules may be obtained from FCV strain 2280 and, in particular, may be derived from DNA sequences coding for the (antigenic portions of) FCV capsid protein of FCV strain 2280. In a further embodiment, the recombinant molecules of the present invention may be fused to DNA sequences of the LacZ gene, which code for β-galactosidase. The recombinant DNA molecules of the present invention may also comprise expression cassettes that have the recombinant (modified) portion of the FCV 2280 capsid gene.

In still another preferred embodiment of the present invention, the modified or recombinant nucleic acid (DNA) sequences may be introduced into a live recombinant carrier and expressed, for example by: (a) transforming host cells (CRFK) with live recombinant carrier; (b) expressing the genome introduced into the expression vector; (c) harvesting the cell culture, and (d) isolating the synthesized capsid protein. Moreover, expression of the fusion proteins by the recombinant DNA molecules may be achieved by any suitable conventional means including, without limitation, use of Crandell-Rees Feline Kidney (CRFK) cells. The CRFK cells may be transfected with plasmids comprising LacZ fusions under the control of the Rous sarcoma retrovirus long terminal repeat promoter (RSVp) (which promoter is known to be able to drive expression of the LacZ gene—in plasmid pRSVLACE—in feline cells) and SV40 early transcript cleavage and polyadenylation sequences. Expression may be validated by immunodetection in extracts of transfected cells by sandwich ELISA using different combinations of antibodies specific to β-galactosidase or to the capsid portion of the fusion protein. Plasmids that may be used in accordance with the present invention include, but are not limited to, pRSVC1LAC, pRSVC2LAC, pRSVC3LAC, pRSVC4LAC, pRSVC5LAC, pRSVC6LAC, pRSVC7LAC, pRSVC8LAC and pRSVC9LAC, whose structures and constructions are discussed in the Examples below. In this context, transient expression of CRFK cells transfected with plasmid pRSV-LACE may be used as a reference.

In this regard, it is noted that such fusions may contain either all regions or sub-regions of the variable segment in order to retain or exclude some of the splicing signals. In addition, some of the remaining splicing sites may be mutated to inactivate them and retain the antigenicity (and/or original amino acid sequence) of the original (heterologous or homologous) polypeptide (such as the amino acid sequence of the capsid protein and/or β-galactosidase).

In still another preferred embodiment, the nucleotide sequences or molecules of the present invention may be introduced in any suitable expression vector with the aim of expression of a polypeptide in susceptible host cells and/or host organisms. In this aspect of the present invention, recombinant expression vectors of the present invention preferably comprise recombinant (modified) DNA sequences that are capable of being transcribed in the nucleus of eukaryotic cells without being altered by the cells' splicing machinery and being introduced into a eukaryotic organism with the use of live recombinant carriers (LRCs). The recombinant vectors may comprise, without limitation, recombinant (modified) DNA sequences that are derived from FCV genes coding for the FCV capsid protein, and preferably derived from FCV strain 2280 coding for the FCV capsid protein. Further, the recombinant expression vectors of the present invention may include, without limitation, live recombinant feline herpes virus-1 (FHV-1) vectors that are useful as live carriers for the development of vaccines for feline calicivirus (FCV) disease.

In accordance with the present invention, the live recombinant feline herpes virus-1 (FHV-1) vectors may be modified to provide the recombinant nucleotide sequences and/or recombinant DNA molecules of the present invention incorporated therein. Preferably, modifications of FHV-1 vectors of the present invention are introduced in a permissive position, i.e., a position or region that may be used for the incorporation of the modification without disrupting essential functions of the vector, such as those necessary for infection or replication.

Further, the recombinant FHV-1 vectors of the present invention may include the (heterologous) recombinant DNA molecules of the present invention flanked by appropriate FHV-1 sequences whereby recombination occurs between sequences of the heterologous recombinant DNA molecules and sequences of the FHV vector. Recombinant viral progeny is thereafter produced in cell culture and can be selected for, by example, genotypically or phenotypically, by hybridization, detecting enzyme activity encoded by a gene co-integrated along with the heterologous recombinant DNA molecule or detecting the antigenic (heterologous or homologous) polypeptide expressed by the recombinant FHV immunologically. Recombinant viruses can also be selected positively based on resistance to compounds such as neomycine, gentamycine, or mycophenolic acid. The selected recombinant FHV can be cultured on a large scale in cell culture where after recombinant FHV containing material or (heterologous or homologous) polypeptides expressed by said FHV can be collected therefrom.

The present invention also comprises cell cultures transformed or infected with the recombinant (FHV-1) vectors described above. Preferred cell cultures of the present invention include, without limitation, Crandell-Rees Feline Kidney (CRFK) cells that have been infected with the recombinant FHV-1 vectors of the present invention. In accordance with the present invention, such recombinant FHV-1 vectors can be grown on cell cultures of feline origin (such as CRFK cells) and harvested by collecting the tissue cell culture fluids and/or cells and the live vaccine prepared therefrom in the form of a suspension or may be lyphophilized.

In a further preferred embodiment, the present invention comprises vaccines, which contain the recombinant expression vectors and/or said recombinant DNA sequences. The vaccines of the present invention may be used for the prevention and treatment of diseases, such as feline calicivirus (FCV) disease. Preferably, the vaccines of the present invention may comprise the recombinant FHV-1 vectors (having the recombinant DNA molecules of the present invention which include the DNA sequences of the present invention of the FCV 2280 capsid gene with the modified splicing sites), in a pharmaceutically-acceptable carrier. It will be appreciated that the recombinant FHV vector of the present invention may also serve as a monovalent or multivalent vaccine. As used herein, the term "pharmaceutically-acceptable carrier" refers to those liquid or solid compositions which are susceptible of being used as an excipient (vehicle) for introducing the vector into an animal to be vaccinated therewith. Examples of such liquid compositions are water, physiological serum, saline phosphate buffers, solutions containing adjuvants, detergents, stabilizers and substances which facilitate transfection, liposome suspensions, virosome suspensions and emulsions. Such liquid compositions may be administered, inter alia, orally, intranasally, oronasally or parentally (i.e., intradermally, subcutaneously or intramuscularly). Solid compositions include microparticles containing an expression vector of the present invention, which are administered by parental or oral routes.

It is well within the ability of a person skilled in the art using routine experimentation to determine the thresholds and therapeutic dosages or frequency at which the vaccines should be administered for any given application or administration route. The useful dosage to be administered will vary according to, inter alia, the age and weight of the animal to be inoculated and the mode of administration. A suitable dosage can be, for example, between about $10^3$–$10^7$ pfu per animal. Vaccination with a live vector vaccine of the present invention is generally followed by replication of an FHV-1 mutant within an inoculated host, in vivo expression of the (heterologous or homologous) polypeptide (such as the FCV capsid protein) along with the FHV polypeptides. The polypeptides (such as the FCV capsid protein) expressed in the inoculated host will then elicit or cause an immune response that will effectively immunize the host against subsequent infection against a specific pathogen (such as the FCV disease).

The efficacy of the vaccines of the present invention to, in vivo, express the fusion (heterologous or homologous) polypeptides (proteins) in feline cells after vaccination with the recombinant viruses and confer protection against FCV disease upon cats, was tested by vaccinating cats with the recombinant viruses C1 and C8 and measuring the seroconversion of the cats against the fusion proteins.

As used herein, the term "mutants", when referring to nucleotides and nucleotide sequences, refers to nucleotides and nucleotides sequences obtained by altering the native or original state (in specific nucleotides) and/or order (in sequences) thereof by means and instrumentalities that are well-known to the skilled artisan. It is to be understood that any suitable mutation may be made to the nucleotides and nucleotide sequences by using routine techniques that are well known so long as the objects and principles of the present invention, as discussed throughout this description, are not offended or compromised.

The techniques, procedures and methods employed herein, including the recombinant DNA technology referred to, the DNA clonings and sequencing techniques and procedures and the methods referred to, the methods, techniques and procedures for obtaining, identifying and isolating the nucleotides and nucleotide sequences referred to and the methods procedures and techniques for isolating desired DNA fragments, combining DNA fragments with appropriate expression signals in appropriate expression vectors; and introducing expression vectors in an appropriate hosts therefor, are those which are described in Molecular Cloning, Laboratory manual, (Sambrook, Fritsch, Maniatis) 2nd edition (1989) and Molecular Cloning, A Laboratory Manual, (Maniatis, Fritsch and Sambrook) Cold Spring Harbor Laboratory (1982), all of which are well-known to those skilled in the art.

Cell and tissue culturing techniques and procedures used herein are those which are described by Doyle, et al., in Cell and Tissue Culture: Laboratory Procedures, John Wiley Publishing (1993).

Dilutions, quantities, etc., which are expressed herein in terms of percentages are, unless otherwise specified, percentages given in terms of percent weight per volume (w/v). As used herein, dilutions, quantities, etc., which are expressed in terms of % (v/v), refer to percentage in terms of volume per volume. As used herein, dilutions, quantities, etc., which are expressed in terms of % (v/w), refer to percentage in terms of volume per weigh. As used herein, dilutions, quantities, etc., which are expressed in terms of % (w/w), refer to percentage in terms of weight per weight.

Temperatures referred to herein are given in degrees centigrade (° C.).

Having described the nucleotide (DNA) sequences of the present invention, the recombinant DNA molecules incorporating such sequences therein, the recombinant vectors incorporating such recombinant DNA molecules therein, the cells cultures infected with such recombinant vectors and the vaccines which comprise such recombinant vectors, the following Examples are now presented for the purposes of illustration and are neither meant to be, nor should they be, read as being restrictive or limiting in any way.

EXAMPLE 1

Propagation of Feline Calicivirus (FCV)

FCV viral strain FCV 2280 MS (which is deposited in the American Type Culture Collection under accession number VR 2555) is grown on Crandell-Reese Feline Kidney cells (CRFK) (deposited in the American Type Cell Culture Collection under accession number CCL94). The cells are grown at 37° C. in an atmosphere having 3% of $CO_2$ and in culture media of: (1) 500 ml of medium 199 with Earle's salts, 2.2 g/l $NaHCO_3$ and L-glutamine(GIBCO); (2) 500 ml of Ham's F12 with L-glutamine (GIBCO); (3) 25 ml of lactalbumin hydrolysate (GIBCO); (4) 25 ml of fetal calf serum (GIBCO); and (5) 5 ml of a fructose solution (conc. of 200 grams of fructose/l). The cells are then infected with approximately 0.01 virus particle per cell at a cell confluence of about 50% to 80%, as visually observed (as used in the Examples herein, 100% confluence is defined as $10^5$ cell/cm of plate) and then incubated for two to three days at 37° C. in an atmosphere having 3% $CO_2$ in culture medium having the same composition as that described above.

EXAMPLE 2

Partial Purification of the FCV Genomic RNA

Supernatants are then decanted from about 2 $10^8$ CRFK cells infected with SAH-2280 MS, obtained as described above in Example 1, when the cytopathic effect is almost complete, as determined by visual observation. The collected supernatant is then clarified by centrifugation at 500 G for 10 minutes and the clarified supernatant is decanted from the resulting pellet. The clarified supernatant is then centrifuged at 25000 RPM (SW 28 BECKMAN rotor) and 4° C. for one hour, and the resulting supernatant is then decanted from the resulting viral particle-containing pellet. The viral particle containing pellet is then resuspended in 10 mM TRIS (tris-(Hydroxymethyl)-aminomethane) (pH 7.5) and 1 mM EDTA (ethylenediaminetetraacetate).

This suspension is then loaded on a cushion of 25% sucrose in 10 mM TRIS (pH 7.5) and 1 mM EDTA and is centrifuged at 25000 RPM (SW 28 rotor) for 2 hours at 4° C., generating a viral pellet. After decanting the supernatant from the resulting pellet, the viral pellet is then resuspended in a mixture of 10 mM TRIS (pH 7.5), 10 mM NaCl, 10 mM EDTA, 0.5% (w/v) SDS (Sodium Dodecyl Sulphate) and 500 $\mu$g proteinase K (BOEHRINGER) per ml of the suspension and incubated for 2 hours at 50° C.

Viral RNA is then purified by successive phenol/chloroform extractions until the aqueous phase is clear. The clear aqueous phase is then subjected to ethanol precipitation. The precipitated FCV genomic viral RNA is then resuspended in ½ ml MilliQ water (MilliQ ZMFQ05001, MILLIPORE).

EXAMPLE 3

Preparation, Cloning, and Sequencing of FCV Capsid Gene cDNA and Identification of Potential Splicing Sites thereof Two cDNA fragments, named CALI14 and CALI23, corresponding to the whole capsid gene sequence, is then obtained by reverse transcription and Polymerase Chain Reaction (PCR) amplification from the precipitated FCV genomic viral RNA obtained as described above in Example 2. The CALI14 cDNA fragment (whose sequence is set forth below) is obtained by reverse transcription of the precipitated FCV genomic viral RNA from Example 2, done in a total volume of 25 $\mu$l, consisting of: 0.5 $\mu$l of the precipitated FCV genomic viral RNA; 10 mM Tris (pH 8.3); 50 mM KCl; 5 mM $MgCl_2$; 1 mM of dATP; 1 mM of dCTP; 1 mM of dGTP; 1 mM of dTTP; and 4 $\mu$M of primer CALI4 (EUROGENTEC), whose sequence is described below. The reaction mixture is then incubated for 5 minutes at 95° C. and then put immediately on ice. Next, 20 units of Moloney Murine Leukemia virus reverse transcriptase (PHARMACIA) and 25 units of RNAse inhibitor (PHARMACIA) are added to the reaction mixture. This mixture is then incubated for 1 hour at 42° C. and finally for 5 minutes at 99° C.

Amplification of the CALI4 cDNA fragment is done by, first, adjusting the above described 25 $\mu$l reaction mixture to a final volume of 100 $\mu$l consisting of reversed transcribed FCV genome viral DNA, 10 mM Tris (pH 8.3), 50 mM KCl, 2 mM $MgCl_2$, 0.25 mM of dNTP and 1 $\mu$M of primers CALI1 (EUROGENTEC) and CALI4 (EUROGENTEC), whose sequences are described below. Amplification is then performed using a thermal cycler (PHARMACIA LKB Gene ATAQ controller) with the following cycle parameters: (1) 95° C. for 2 minutes; (2) 60° C. for 1 minute; and (3) 72° C. for 2 minutes. The cycle is repeated 40 times and followed by incubation for 10 minutes at 72° C. The amplified CALI14 cDNA fragment obtained in this fashion is about 0.7 kilo basepairs (kbp).

The CALI23 cDNA fragment is obtained in the same manner as described above for the CALI14 cDNA fragment with the exceptions that reverse transcription is performed with primer CALI2 at a concentration of 1 $\mu$M and amplification is performed with primers CALI2CLON (EUROGENTEC) and CALI3 (EUROGENTEC), at a final concentration of 0.25 $\mu$M with the same cycle parameters as specified above: (1) 95° C. for 2 minutes; (2) 60° C. for 30 seconds; and (3) 72° C. for 2 minutes. The amplified CALI23 cDNA fragment is about 1.5 kbp.

The sequences of the various primers referred to above are as follows:

CALI1
5' GATGTGTTCGAAGTTTGAGCATG 3' (SEQ ID NO: 1)

CALI2
5' GTGTTCGTGACAGTATCAATCAAGCCCAAAATTGAATTC 3' (SEQ ID NO: 2)

CALI2CLON
5' CGCGGATCCGTCGACCGCATGCGTGTTCGTGACAGTATCAATCAAGCCCAAAATTGAATTC 3' (SEQ ID NO: 3)

CALI3
5' GGGAAAAGAGTTGACTCTGAGTGGGAGGC 3' (SEQ ID NO: 4)

CALI4
5' CACCAGAGCCAGAAATAGAGAACCTAAC 3' (SEQ ID NO: 5)

Plasmid pCALI, having the whole capsid gene sequence, is then constructed from the CALI14 and CALI23 cDNA fragments, as follows. First, the CALI14 cDNA fragment is treated with T4 DNA polymerase (PHARMACIA). Next, the CALI14 cDNA fragment is cloned in plasmid pBSLK1 (described in European Patent Application N° 517,292) which has been previously digested with SmaI, resulting in plasmid pCALI14. The CALI23 cDNA fragment is then double digested with SphI and BsmI and cloned into plasmid pCALI14, which has been previously subjected to a double digestion with SphI and BsmI, resulting in plasmid pCALI.

The complete nucleotide sequence of the capsid gene is determined using double-stranded plasmid pCALI as template and primers (EUROGENTEC) made either to the vectors just outside the insert to be sequenced or to previously obtained sequences inside the insert. Sequencing is performed in a chain termination reaction using T7 polymerase (PHARMACIA) and $S^{35}$dATP (AMERSHAM). The sequence obtained is set forth in FIG. 1 (SEQ ID NO: 23).

The variable region of the capsid gene is then identified by comparison with known published capsid gene sequences of feline calicivirus strains (Virus Research 33 (1994) p. 39–53 and J. Of Gen. Virology 74 (1993) pp. 2519–2524). From this comparison, it is determined that the variable region of the capsid gene of feline calicivirus strain FCV 2280 is found from nucleotide 1183 to 1584, inclusive, as noted in FIG. 1 (SEQ ID NO: 23). This portion of the capsid gene is shown in FIG. 2 (SEQ ID NO: 24).

Those portions of the variable region of the capsid gene (SEQ ID NO: 24) that match the consensus splicing sequences noted above are then identified by comparison with sequences of known published consensus splicing sites which are set forth above (See, P. Senapathy, et al., Methods in Enzymology, Vol. 183, pps. 252–278 (1993)). From this comparison, consensus splicing sites that are present in the variable region of the capsid gene of feline calicivirus strain FCV 2280 are identified. These identified consensus sequences are set forth below in Table 1, wherein bold characters represent nucleotides which match with the consensus splicing sequences; and further wherein position refers to the nucleotide sequence of FIG. 2 (SEQ ID NO: 24).

TABLE 1

| Donor Sites | | Acceptor Sites | |
|---|---|---|---|
| Label, Position | Sequence | Label, Position | Sequence |
| D1, 1–6 | /**GTTAGT** | A1, 58–70 | **CCCGGTATTCCAG**/ (SEQ ID NO: 6) |
| D2, 8–13 | **AAA/GTG** | A2, 103–116 | **CTTACCCCTGCAG/G** (SEQ ID NO: 7) |
| D3, 13–19 | **G/GTGGGT** | A3, 272–285 | **TTTTATCACCACAG**/ (SEQ ID NO: 8) |
| D4, 33–37 | **AG/GTG** | A4, 341–355 | **TTGTTGTGTACCAG/G** (SEQ ID NO: 9) |
| D5, 113–121 | **CAG/GTAATT** | | |
| D6, 209–217 | **AAA/GTATGT** | | |
| D7, 247–251 | **G/GTGA** | | |
| D8, 296–302 | **AAG/GTAA** | | |
| D9, 361–368 | **CAC/GTGGG** | | |

EXAMPLE 4

Construction of pRSVCALI Intermediate Plasmid Having FCV Capsid Gene Expression Cassette An intermediate plasmid pRSVCALI is then constructed having an FCV-capsid gene expression cassette. The intermediate expression plasmid pRSVCALI contains the Rous sarcoma retrovirus (RSV) long terminal repeat promoter and the SV40 late transcript cleavage and polyadenylation signals.

PRSVCALI is constructed by the insertion of the capsid gene cDNA, obtained from pCALI, as described in Example 3, in the intermediate expression plasmid pRSVpolyAL (the structure and construction of which is described in PCT/EP94/02990).

Insertion of the capsid gene cDNA from pCALI in the intermediate plasmid pRSVpolyAL is performed by, first, obtaining uracilated single-stranded pCALI DNA and then subjecting this uracilated single-stranded pCALI DNA to site-directed mutagenesis following the supplier recommendations (BioRad Muta-Gene Phagemid In Vitro Mutagenesis Kit), generating pCALIMUT. Mutagenesis is performed using the four synthetic primers (EUROGENTEC), as follows:

CALIMUT1

5' GGGCGAATTTCGAGCTCGGTACCAGATCTCTCGAAGTTCCAACATGTGCTCAACCTGCGC 3' (SEQ ID NO: 10)

CALIMUT2

5' CTATGGCTGGGACCCCCACTTTAG 3' (SEQ ID NO: 11)

CALIMUT3

5' GTGGGACTGTGACCAGTCTCCACTAC 3' (SEQ ID NO: 12)

CALIMUT4

5' CTGTCACGAACACGGATCCAAGCTTTTGTTCCC 3' (SEQ ID NO: 13)

Next, pCALIMUT is subjected to a double digestion by BglII and BamHI and the 2.1 kbp fragment is isolated therefrom. Similarly, the plasmid pRSVpolyAL is digested with BglII. The 2.1 kbp BglII-BamHI fragment from pCALIMUT is then inserted into the BglII site of the pRSVpolyAL, generating plasmid pRSVCALI.

EXAMPLE 5

Construction of pdTKRSVCLAC Cotransfection Plasmid

A cotransfection plasmid, pdTKRSVCLAC is then constructed containing both an FCV capsid gene and a LacZ expression cassette. pdTKRSVCLAC is constructed for use in the cotransfection of feline cells with FHV-1 viral DNA.

First, plasmid pHCMVLACE (whose structure and construction are described in PCT/EP94/02990) is subjected to a double digestion with BclI and BamHI and the 3.8 kbp LacZ expression cassette isolated therefrom.

The plasmid pRSVCALI, obtained as described above in Example 4, is digested with BamHI.

The LacZ expression cassette, contained on a 3.8 kbp BclI-BamHI fragment of pHCMVLACE, is then inserted into the BamHI site of pRSVCALI, generating the plasmid pRSVCLAC.

The plasmid pRSVCLAC is then subjected to a double digestion with BclI and BamHI and the 6.6 kbp BclI-BamHI fragment is isolated therefrom.

Plasmid pdTK (whose structure and construction are described in PCT/EP94/02990) is then subjected to a double digestion with BamHI.

The 6.6 kbp BclI-BamHI fragment is then cloned into the BamHI site of intermediate transfer plasmid pdTK, thereby generating the cotransfection plasmid pdTKRSVCLAC.

EXAMPLE 6

Production of an FHV-1 Live Recombinant Carrier Having the Calicivirus Capsid Gene and the LacZ Gene A live recombinant FHV-1 carrier (containing the capsid and the LacZ gene) is then obtained by cotransfection (using the procedure described in PCT/EP94/02990) of CRFK cells with purified FHV-1 DNA (as described in PCT/EP94/02990) using the cotransfection plasmid pdTKRSVCLAC, which is obtained as described in Example 5, giving a mixture of wild-type and recombinant FHV-1 viruses.

To achieve the production of the Live Recombinant Carrier (LRC), first a recombinant plaque is purified based on the expression of the LacZ gene (using the procedure as described in PCT/EP94/02990).

Next, expression of the capsid gene is evaluated by a sandwich ELISA on crude extracts of CRFK cells infected with the purified recombinant. CRFK cells at 80% confluence (visually observed) are infected with the recombinant FHV-1 at a multiplicity of infection of 5 to 10.

After 24 hours (when the cytopathic effect is almost complete), cells and growth medium are subjected to one cycle of freezing and thawing. Fifty microliters of these crude extracts are analyzed in ELISA using, as the first antibody, the monoclonal antibody FCV 2-1A or FCV 2-2A for capture of the antigen and, as the second antibody, a polyclonal anti-serum of a cat immunized with calicivirus strain FCV 2280. (Monoclonal antibodies FCV 2-1A and FCV 2-2A are directed against the variable region of the calicivirus capsid protein and are obtainable from CUSTOM MONOCLONALS, WA 98020, USA). Detection was performed with an alkaline phosphatase-conjugated goat anti-cat IgG (Jackson ImmunoResearch Laboratories, Inc.).

No expression of the capsid protein is detected.

EXAMPLE 7

Construction of Plasmids Having Expression Cassette for Feline Calicivirus CAPSID/β-Galactosidase Fusion Genes A. Construction of plasmid pRSVC1LAC First, using plasmid pRSVCALI (described in Example 4) as template and synthetic primers (EUROGENTEC) F1A and F1B (whose sequences are described below) an approximately 0.37 kbp DNA fragment is amplified by PCR using standard techniques and with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

The sequences of F1A and F1B are as follows:

F1A

5' TTGGGATAGGTGTTCACCATGGCAACTGACTACATTG 3' (SEQ ID NO: 14)

F1B

5' CATTGCCCACGTGGACGTCATTCCAGCTAGCATCCTGGTACA 3' (SEQ ID NO: 15)

This 0.37 kbp DNA fragment is then subjected to a double digestion with NcoI and AatII. A resulting 0.34 kbp fragment is then isolated therefrom and cloned into the 5.7 kbp fragment of plasmid pRSVLACE (whose structure and construction are described in PCT/EP94/02990), which is obtained by subjecting pRSVLACE to a double digestion with NcoI and AatII, generating plasmid pRSVC1DLAC.

Then, using plasmid pRSVLACE as a template and synthetic primers (EUROGENTEC) FL1A and FL1B described below, an approximately 0.86 kbp DNA fragment is amplified by PCR using standard techniques and with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

The sequences of FLAC1 and FLAC2 are as follows:

FLAC1

5' CACCAGATCTCACCATGGCTAGCGCCGTCGTTTTACAACG 3' (SEQ ID NO: 16)

FLAC2

5' CCACCACGCTCATCGATAATTTCACCGCCGAAAGGCGCG 3' (SEQ ID NO: 17)

The approximately 0.86 kbp DNA fragment is then subjected to a double digestion with NheI and AatII and a resulting 0.62 kbp NheI-AatII fragment is isolated therefrom. Plasmid pRSVC1DLAC is then subjected to a double digestion with NheI and AatII and the 6.0 kbp fragment isolated therefrom. The 0.62 kbp NheI-AatII fragment is then cloned into the 6.0 kbp fragment of plasmid pRSVC1DLAC, thereby generating plasmid pRSVC1LAC.

B. Construction of plasmid pRSVC2LAC

First, using plasmid pRSVCALI (described in Example 4) as a template and synthetic primers (EUROGENTEC) F2A and F2B (whose sequences are described below) an approximately 0.46 kbp DNA fragment is amplified by PCR using standard techniques and with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

The sequences of F2A and F2B are as follows:

F2A

5' CCAATAACTGTTACACACCATGGTTAGTGAAAGTGG 3' (SEQ ID NO: 18)

F2B

5' GTGTAACCAAGAAGGACGTCATTCCAGCTTGCAAGGGTGACATCGG 3' (SEQ ID NO: 19)

This approximately 0.46 kbp DNA fragment is then subjected to a double digestion with NcoI and AatII and a resulting 0.43 kbp NcoI-AatII fragment is isolated therefrom. Plasmid pRSVLACE, which is described in PCT/EP94/02990, is then subjected to a double digestion with NcoI and AatII and a resulting 5.7 kbp NcoI-AatII fragment is isolated therefrom. The 0.43 kbp NcoI-AatII fragment is then cloned into the 5.7 kbp NcoI-AatII fragment, generating plasmid pRSVC2DLAC.

Then, a DNA fragment of approximately 0.86 kbp is amplified by PCR using plasmid pRSVLACE as a template and synthetic primers (EUROGENTEC) FL1A and FL1B described above. The amplification is performed with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

The approximately 0.86 kbp DNA fragment is then subjected to a double digestion with NheI and AatII and a resulting 0.62 kbp NheI-AatII fragment is isolated therefrom. Plasmid pRSVC2DLAC is also subjected to a double digestion with NheI and AatII and the 6.1 kbp fragment isolated therefrom. The 0.62 kbp NheI-AatII fragment is then cloned into the 6.1 kbp fragment of plasmid pRSVC2DLAC, thereby generating plasmid pRSVC2LAC.

C. Construction of plasmid pRSVC3LAC

First, using plasmid pRSVCALI (described in Example 4) as a template and synthetic primers (EUROGENTEC) F2A and F1B described above, an approximately 0.41 kbp DNA fragment is amplified by PCR using standard techniques and with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

This approximately 0.41 kbp DNA fragment is then subjected to double digestion with NcoI and AatII and a resulting 0.38 kbp NcoI-AatII fragment is isolated therefrom. This 0.38 kbp NcoI-AatII fragment is then cloned into the 5.7 kbp NcoI AatII fragment of plasmid pRSVLACE (described in PCT/EP94/02990), which is obtained by subjecting pRSVLACE to a double digestion with NcoI and AatII, thereby generating plasmid pRSVC3DLAC.

Then, using plasmid pRSVLACE as template and synthetic primers (EUROGENTEC) FL1A and FL1B described above, a DNA fragment of approximately 0.86 kbp is amplified by PCR using standard techniques and with the following cycle parameters: (1) 95° C. for 2 minutes; (2) 55° C. for 1 minute; (3) 72° C. for 2 minutes. The cycle is repeated 30 times and followed by incubation for 10 minutes at 72° C.

The approximately 0.86 kbp DNA fragment is then subjected to a double digestion with NheI and AatII and a resulting 0.62 kbp NheI-AatII fragment is isolated therefrom. Plasmid pRSVC3DLAC, was then subjected to a double digestion with NheI and AatII and the 6.1 kbp fragment isolated therefrom. The 0.62 kbp NheI-AatII fragment was then cloned into the 6.1 kbp fragment of plasmid pRSVC3DLAC, generating plasmid pRSVC3LAC.

D. Construction of plasmid pRSVC4LAC

First, using plasmid pRSVCALI (described in Example 4) as template and synthetic primers (EUROGENTEC) F1A and F2B described above, an approximately 0.45 kbp DNA fragment was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The approximately 0.45 kbp DNA fragment was then subjected to a double digestion with NcoI and AatII and a resulting 0.42 kbp NcoI-AatII fragment was isolated therefrom. This 0.42 kbp NcoI-AatII fragment was then cloned into the 5.7 kbp fragment of plasmid pRSVLACE (described in PCT/EP94/02990) which had been obtained by previously subjecting pRSVLACE to a double digestion with NcoI and AatII, generating plasmid pRSVC4DLAC.

Then, using plasmid pRSVLACE as template and synthetic primers (EUROGENTEC) FL1A and FL1B described above a DNA fragment of approximately 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The approximately 0.86 kbp DNA fragment was then subjected to a double digestion with NheI and AatII and a resulting 0.62 kbp NheI-AatII fragment was isolated therefrom. Plasmid pRSVC4DLAC, was then subjected to a double digestion with NheI and AatII and the 6.1 kbp fragment isolated therefrom. The 0.62 kbp NheI-AatII fragment was then cloned into the 6.1 kbp fragment of plasmid pRSVC4DLAC, generating plasmid pRSVC4LAC.

E. Construction of plasmid pRSVC5LAC

First, uracilated single-stranded DNA from plasmid pRSVCALI, described above in Example 4, was subjected to site-directed mutagenesis following the supplier recommendations (BioRad Muta-Gene Phagemid In Vitro Mutagenesis Kit). Mutagenesis was done using the two synthetic primers (EUROGENTEC) described below:

MUTVAR1

5' CAATGTAGTCAGTTGCTACGCCGATC-CCAAGCTTTGACCCTCCGCTCTCAC-TAACTGTAACAG 3' (SEQ ID NO: 20)

MUTVAR2

5' GCTGGTTGTAATTGCATAGTTGCCCGC-CGGTGTTAGCTTTTCAGGAATTG 3' (SEQ ID NO: 21)

The resulting plasmid is called pRSVCALIMUT.

Using plasmid pRSVCALIMUT as template and synthetic primers (EUROGENTEC) F2A and F1B described above, a DNA fragment of about 0.41 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.41 kbp DNA fragment was then subjected to a double digestion with NcoI and AatII and the resulting 0.38 kbp fragment cloned into a 5.7 kbp fragment of plasmid pRSVLACE (described in PCT/EP94/02990) which had been obtained by previously subjecting pRSVLACE to a double digestion with NcoI and AatII. The resulting plasmid was pRSVC5DLAC.

Then, using plasmid pRSVLACE as template and synthetic primers (EUROGENTEC) FL1A and FL1B described above, a DNA fragment of about 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.86 kbp DNA fragment was then subjected to a double digestion with NheI and AatII and the resulting 0.62 kbp fragment isolated therefrom. Plasmid pRSVC5DLAC, was subjected to a double digestion with NheI and AatII and the 6.1 kbp fragment isolated therefrom. The 0.62 kbp NheI-AatII fragment was then cloned into the 6.1 kbp fragment of plasmid pRSVC5DLAC, generating plasmid pRSVC5LAC.

F. Construction of plasmid pRSVC6LAC

First, using plasmid pRSVCALIMUT as template and synthetic primers (EUROGENTEC) F2A and F2B described above, a DNA fragment of about 0.46 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.46 kbp DNA fragment was subjected to a double digestion with NcoI and AatII and the resulting 0.43 kbp fragment obtained therefrom was cloned into the 5.7 kbp fragment of plasmid pRSVLACE (described in PCT/EP94/02990) which had been previously obtained by subjecting pRSVLACE to a double digestion with NcoI and AatII. The resulting plasmid is pRSVC6DLAC.

Then, using plasmid pRSVLACE as template and synthetic primers (EUROGENTEC) FL1A and FL2B described above, a DNA fragment of about 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.86 kbp DNA fragment was then subjected to a double digestion with NheI and AatII and the resulting 0.62 kbp fragment isolated therefrom. Plasmid pRSVC6DLAC, was subjected to a double digestion with NheI and AatII and the 6.1 kbp fragment isolated therefrom. The 0.62 kbp NheI-AatII fragment was then cloned into the 6.1 kbp fragment of plasmid pRSVC6DLAC, generating plasmid pRSVC6LAC.

G. Construction of plasmid pRSVC7LAC

First, using plasmid pRSVCALIMUT as template and synthetic primers (EUROGENTEC) F1B described above and F7 described below, a DNA fragment of about 0.41 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The sequence of F7 is the following:

F7

5' CCAATAACTGTTACACACCATGGTTAGT-GAGAGCGGAGGGTCAAAGCTTGGG 3' (SEQ ID NO: 22)

The 0.41 kbp DNA fragment was then subjected to a double digestion with NcoI and AatII and the resulting 0.38 kbp fragment cloned into the 5.7 kbp fragment of plasmid pRSVLACE (described in PCT/EP94/02990) which had been obtained by previously subjecting pRSVLACE to a double digestion with NcoI and AatII. The resulting plasmid was pRSVC7DLAC.

Then, using plasmid pRSVLACE as template and synthetic primers (EUROGENTEC) FL1A and FL1B described above, a DNA fragment of about 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.86 kbp DNA fragment was then subjected to a double digestion with NheI and AatII and the resulting 0.62 kbp fragment isolated therefrom. Plasmid pRSVC7DLAC, was subjected to a double digestion with NheI and AatII and the 6.1 kbp fragment isolated therefrom. The 0.62 kbp NheI-AatII fragment was then cloned into the 6.1 kbp fragment of plasmid pRSVC7DLAC, generating plasmid pRSVC7LAC.

H. Construction of plasmid pRSVC8LAC

Using plasmid pRSVCALIMUT as template and synthetic primers (EUROGENTEC) F7 and F2B described above, a DNA fragment of about 0.46 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.46 kbp DNA fragment was subjected to a double digestion with NcoI and AatII and the resulting 0.43 kbp fragment cloned into the 5.7 kbp fragment of plasmid pRSVLACE (described in PCT/EP94/02990) which had previously been obtained by subjecting pRSVLACE to a double digestion with NcoI and AatII. The resulting plasmid was pRSVC8DLAC.

Then, using plasmid pRSVLACE as template and synthetic primers (EUROGENTEC) FL1A and FL1B described above, a DNA fragment of about 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.86 kbp DNA fragment was then subjected to a double digestion with NheI and AatII and the resulting 0.62 kbp fragment isolated therefrom. Plasmid pRSVC8DLAC, was also subjected to a double digestion with NheI and AatII and the 6.1 kbp fragment isolated therefrom. The 0.62 kbp NheI-AatII fragment was then cloned into the 6.1 kbp fragment of plasmid pRSVC8DLAC, generating plasmid pRSVC8LAC.

I. Construction of plasmid pRSVC9LAC

First, using plasmid pRSVCALIMUT as template and synthetic primers (EUROGENTEC) F1A and F1B described above, a DNA fragment of about 0.37 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.37 kbp DNA fragment was then subjected to a double digestion with NcoI and AatII and the resulting 0.34 kbp fragment cloned into the 5.7 kbp fragment of plasmid pRSVLACE (described in PCT/EP94/02990) which had been obtained by previously subjecting pRSVLACE to a double digestion with NcoI and AatII. The resulting plasmid was pSRVC9DLAC.

Then, using plasmid pRSVLACE as template and synthetic primers (EUROGENTEC) FL1A and FL1B described above, a DNA fragment of about 0.86 kbp was amplified by PCR using standard techniques and with the following cycle parameters: (1) 95° C. for 2 minutes; (2) 55° C. for 1 minute; (3) 72° C. for 2 minutes. The cycle was repeated 30 times and followed by incubation for 10 minutes at 72° C.

The 0.86 kbp DNA fragment was then subjected to a double digestion with NheI and AatII and the resulting 0.62 kbp fragment isolated therefrom. Plasmid pRSVC9DLAC, was also subjected to a double digestion with NheI and AatII and the 6.1 kbp fragment isolated therefrom. The 0.62 kbp NheI-AatII fragment was then cloned into the 6.1 kbp fragment of plasmid pRSVC9DLAC, generating plasmid pRSVC9LAC.

EXAMPLE 8

Transient Expression in Transfected Feline Cells of LacZ Gene and FCV Capsid/LacZ Fusion Genes Transient expression of the LacZ gene and the feline calicivirus capsid/LacZ fusion genes was evaluated in CRFK cells transfected, respectively, with plasmid pRSVLACE (described in PCT/EP94/02990) or each of the final plasmids described in Example 7 (plasmids pRSVC1LAC, pRSVC2LAC, pRSVC3LAC, pRSVC4LAC, pRSVC5LAC, pRSVC6LAC, pRSVC7LAC, pRSVC8LAC and pRSVC9LAC).

Each of the ten transfections were performed with Lipofectin® (GIBCO BRL) following the supplier recommendations. CRFK cells were transfected in respective multidish 6 well plates (NUNCLON®, NUNC A/S, Denmark). Each well was seeded with 7 $10^5$ cells in the medium described above in Example 1 from which the serum had been omitted. The plates were then incubated for 30 to 60 minutes at 37° C. in an atmosphere having 3% $CO_2$, until cells were attached to the plates (as visually observed).

The culture medium was then replaced by the same medium to which had been added respective 40 $\mu$g samples of the respective plasmid DNAs and respective 40 $\mu$g samples of Lipofectin®. Total volume was 2 ml. Duration of transfection was 5 hours at 37° C. in an atmosphere having 3% $CO_2$.

After transfection, 2 ml of growth medium with serum was added to each well and the plates were then incubated for 24 hours at 37° C. in an atmosphere having 3% $5CO_2$. Each transfection was done in triplicate. Then, the medium was removed and 500 $\mu$l of phosphate buffer (PBS, Dulbecco's phosphate buffer saline, without calcium and magnesium; GIBCO BRL) was added to the cells of each well.

The cells in PBS medium were then subjected to a cycle of freezing and thawing. The cell lysates of each triplicate transfection were then pooled and used for transient expression analysis.

A series of twofold dilutions (in PBS) of the cell lysates were done and 50 μl of each dilution were analyzed by a sandwich ELISA for the production of the capsid/β-galactosidase fusion protein. A rabbit polyclonal anti-β-galactosidase antiserum (CAPPEL™ Research Products) was used for the capture of the fusion protein and a monoclonal anti-β-galactosidase antibody (BOEHRINGER-MANNHEIM) was used as the second antibody. Detection was done with an alkaline phosphatase-conjugated goat anti-mouse IgG (Jackson ImmunoResearch Laboratories, Inc.) and Disodium p-Nitrophenyl Phosphate (SIGMA®) as substrate.

Development of the reaction was followed spectrophotometrically at 405 nm (TITERTEK) for a period of 30 to 60 minutes.

Table 2 summarizes the level of expression and the characteristics of the different fusion genes with regard to the capsid portion sequence fused to the LacZ gene and mutations introduced to inactivate splicing signals, wherein: CnLAC (n=1, 9) designates transfection done with plasmid pRSVCnLAC (n=1, 9); LacZ, designates transfection done with plasmid pRSVLACE; Position refers to the sequence in FIG. 2 (SEQ ID NO: 24); Expression has been measured by an ELISA specific to β-galactosidase and is indicated as percentage of the transfection giving the highest optical density (C7LAC fusion=100%); and Position refers to the sequence in FIG. 2 (SEQ ID NO: 24).

TABLE 2

Characteristics of the Capsid/LacZ Fusion Genes

| Label | Position | Splicing Sites Excluded | Mutated Splicing Sites | Expression (%) |
|---|---|---|---|---|
| C1LAC | 40–360 | D1→D4, D9 | none | 64 |
| C2LAC | 1–402 | none | none | 5 |
| C3LAC | 1–360 | D9 | none | 4 |
| C4LAC | 40–402 | D1→D4 | none | 42 |
| C5LAC | 1–360 | D9 | D4, D5, A2 | 77 |
| C6LAC | 1–402 | none | D4, D5, A2 | 70 |
| C7LAC | 1–360 | D9 | D2, D3, D4, D5, A2 | 100 |
| C8LAC | 1–402 | none | D2, D3, D4, D5, A2 | 70 |
| C9LAC | 40–360 | D1→D4, D9 | D5, A2 | 88 |
| LacZ | — | — | — | 70 |

Similar results were obtained when detection was performed in a sandwich ELISA using the rabbit polyclonal anti-β-galactosidase antiserum (CAPPEL™ Research Products) for capture of the fusion protein and as second antibody, monoclonal antibody FCV 2-1A or FCV 2-2A, in the same manner as described above in Example 6.

From this data, it is apparent that expression of the fusion genes is negatively affected by the presence of splicing signals located in the sequence coding for the capsid part of the fusion. Removal or specific mutagenesis of some of these signals can lead to a 25-fold increase in expression of the fusion protein (fusion C7LAC in comparison to fusion C3LAC). Inactivation of signals contained within the 120 first nucleotides (D1→D5) results in the highest increase of expression among the different combinations tested. Nevertheless, it is expected that inactivation of the remaining sites can increase expression to an even higher level.

EXAMPLE 9

Construction of pdTKRSVC1LAC and pdTKRSVC8LAC Cotransfection Plasmids

Plasmids pdTKRSVC1LAC and pdTKRSVC8LAC containing, respectively, the C1LAC and C8LAC fusion gene expression cassettes, were constructed for the cotransfection of feline cells with FHV-1 viral DNA (as described below).

Plasmid pdTKRSVC1LAC was constructed by, first, digesting plasmid pRSVC1LAC (described in Example 7) with BclI and BamHI and a 4.1 kbp BclI-BamHI fragment was isolated therefrom. The 4.1 kbp BclI-BamHI fragment was then inserted in intermediate transfer plasmid pdTK (described in PCT/EP94/02990), which had been previously digested with BamHI, generating plasmid pdTKRSVC1LAC.

Plasmid pdTKRSVC8LAC was constructed by, first, digesting plasmid pRSVC8LAC (described in Example 7) with BclI and BamHI and a 4.1 kbp BclI-BamHI fragment was isolated therefrom. The 4.1 kbp BclI-BamHI fragment was then inserted in intermediate transfer plasmid pdTK, which had been previously digested with BamHI, generating plasmid pdTKRSVC8LAC.

EXAMPLE 10

Production of FHV-1 Live Recombinant Carriers Having the C1LAC and C8LAC Fusion Genes Two live recombinant carriers were obtained by cotransfection (as described in PCT/EP94/02990, Example 17) of CRFK cells (as described above) with purified FHV-1 DNA and cotransfection plasmid pdTKRSVC1LAC (described in Example 9) or pdTKRSVC8LAC (described in Example 9).

Recombinant plaques were purified based on the expression of the β-galactosidase activity (as described in PCT/EP94/02990, Example 17) of the fusion genes. Two purified recombinant FHV-1 viruses, named C1 and C8, were obtained from cotransfection with FHV-1 viral DNA of, respectively, plasmid pdTKRSVC1LAC and pdTKRSVC8LAC.

Expression of the fusion genes was confirmed, as described in Example 6, by a sandwich ELISA on crude extracts of CRFK cells infected with each of the purified recombinants.

Large stocks of recombinant viruses C1 and C8 were then produced by infection of CRFK cells at 80% confluence (visually observed) and a multiplicity of infection of 0.01. After 48 to 72 hours, when cytopathic effect was almost complete, the cell suspension was clarified by centrifugation at 500 g for 10 minutes. The supernatant, containing the recombinant virus, was collected and stored at −80° C. These stocks were used for further vaccination experiments.

The two recombinant FHV-1 vectors (having the recombinant DNA molecules of the present invention which include the DNA sequences of the present invention of the FCV 2280 capsid gene with the modified splicing sites) were used to determine if the splicing signals were also effectively inactivated in the context of feline cells infected with recombinant viruses having the fusion genes. Both viruses expressed the fusion proteins as determined by ELISA and Western blot analyses, thereby indicating that splicing signals are also effectively inactivated in the context of feline cells infected with recombinant viruses having the fusion genes.

EXAMPLE 11

Vaccination of Cats with FHV-1 Live Carriers C1 and C8

This example was designed to evaluate in vivo expression and immunogenicity of the fusion proteins C1LAC and C8LAC after vaccination of cats with recombinant FHV-1 C1 and C8, respectively.

Specific-pathogen-free (SPF) cats of about 10 weeks of age were intranasally vaccinated twice three weeks apart with ca. $10^{5.5}$ $TCID_{50}$ per dose of either recombinant C1 (C1 group, 5 cats), obtained as described in Example 10, or recombinant C8 (C8 group, 5 cats), obtained as described in Example 10, or recombinant FHV-1 TKLAC, described in PCT/EP94/02990, (TKLAC group, 5 cats). FHV-1 recombinant TKLAC carries the LacZ gene, under the control of the human cytomegalovirus (HCMV) immediate early gene promoter. Inoculation of the recombinant viruses C1, C8 and TKLAC was done by applying 0.5 ml of the viral suspension in each nostril.

All the specimens of each of the three groups were then challenged oronasally, 3 weeks after the second vaccination. These challenges were done by inoculation with ca. $10^6$ $TCID_{50}$ of the virulent calicivirus strain F9 by giving 0.5 ml of the viral suspension orally and by applying 0.25 ml of the viral suspension in each nostril.

Oronasal secretions were taken from all the specimens of each of the three groups and analyzed by ELISA for the presence of secreted immunoglobulin A (sIgA) specific to calicivirus or β-galactosidase.

Blood samples were also taken and analyzed for seroneutralizing titers against calicivirus strain F9 and FCV 2280 as well as for the presence of immunoglobulin G (IgG) specific to strain F9.

Table 3 summarizes the ELISA analyses of oronasal secretions. The values represent mean optical density×1000. The oronasal secretions were tested for sIgA specific to β-galactosidase and for sIgA specific to calicivirus strain F9. Day refers to the time after the first vaccination which is day 1. Second vaccination was done on day 21 and challenge on day 42.

TABLE 3

| | Anti-FCV Group | | | Anti-β-galactosidase Group | | |
|---|---|---|---|---|---|---|
| Day | C1 | C8 | TKLAC | C1 | C8 | TKLAC |
| 2 | 0 | 0 | 0 | 108 | 109 | 113 |
| 7 | 108 | 110 | 0 | 462 | 287 | 442 |
| 14 | 163 | 142 | 0 | 536 | 404 | 486 |

TABLE 3-continued

| | Anti-FCV Group | | | Anti-β-galactosidase Group | | |
|---|---|---|---|---|---|---|
| Day | C1 | C8 | TKLAC | C1 | C8 | TKLAC |
| 22 | 275 | 284 | 0 | 417 | 312 | 428 |
| 28 | 235 | 234 | 0 | 511 | 392 | 511 |
| 35 | 165 | 147 | 0 | 222 | 174 | 249 |
| 42 | 113 | 134 | 0 | 121 | 107 | 131 |
| 45 | 89 | 73 | 0 | 114 | 115 | 114 |
| 49 | 591 | 628 | 44 | 103 | 102 | 107 |
| 52 | 312 | 415 | 144 | 105 | 118 | 111 |
| 56 | 319 | 241 | 303 | 99 | 110 | 105 |
| 59 | 66 | 100 | 336 | 105 | 108 | 103 |
| 63 | 121 | 91 | 311 | 104 | 105 | 99 |

Table 4 summarizes the ELISA analyses of serum IgG. The values represent mean optical density×1000. The sera were tested for IgG specific to calicivirus strain F9. Day refers to the time after the first vaccination which is day 1. Second vaccination was done on day 21 and challenge on day 42.

TABLE 4

| | Group | | |
|---|---|---|---|
| Day | C1 | C8 | TKLAC |
| 1 | 0 | 0 | 0 |
| 14 | 93 | 76 | 0 |
| 21 | 34 | 37 | 0 |
| 35 | 397 | 510 | 0 |
| 42 | 325 | 440 | 0 |
| 63 | 1290 | 1416 | 1531 |

Results presented in Table 3 and Table 4 demonstrate that recombinant C1 and C8 replicate in SPF cats and induced both systemic and mucosal antibody responses against FCV. This shows that the C1LAC and C8LAC fusions genes are expressed in feline cells infected in vivo with FHV-1 recombinants C1 and C8 respectively.

Those skilled in the art will recognize, or be able to ascertain, using no more than routine experimentation, many equivalents to the specific preferred embodiments that are described above. Such equivalents are intended to be encompassed in the scope of the following claims.

What is claimed is:

1. A method for obtaining an isolated nucleotide sequence that is cloned into a vector and transcribed in a nucleus of an eukaryotic cell without being altered by splicing machinery found within the nucleus, the method comprising:

modifying a consensus splicing site of a nucleotide sequence comprising a feline calicivirus C gene so that said consensus splicing site is inactive.

2. The method of claim 1, wherein the nucleotide sequence codes for the feline calicivirus (FCV) C gene of FCV strain 2280 (ATCC designation VR-2555).

3. The method of claim 1, wherein the consensus splicing site is a member selected from the group consisting of D1, which represents nucleotide residues 1–6 of SEQ ID NO:24, D2, which represents nucleotide residues 8–13 of SEQ ID NO:24, D3, which represents nucleotide residues 13–19 of SEQ ID NO:24, D4, which represents nucleotide residues 33–37 of SEQ ID NO:24, D5, which represents nucleotide residues 113–121 of SEQ ID NO:24, D6, which represents nucleotide residues 209–217 of SEQ ID NO:24, D7, which represents nucleotide residues 247–251 of SEQ ID NO:24, D8, which represents nucleotide residues 296–302 of SEQ ID NO:24, D9, which represents nucleotide residues 361–368 of SEQ ID NO:24, A1, which is represented by nucleotide SEQ ID NO:6, A2, which is represented by nucleotide SEQ ID NO:7, A3, which is represented by nucleotide SEQ ID NO:8, and A4, which is represented by nucleotide SEQ ID NO:9.

4. The method according to claim 1, wherein the consensus splicing site is mutated.

5. The method according to claim 1, wherein the consensus splicing site is in the variable region of feline calicivirus (FCV) capsid protein, and wherein said nucleotide sequence comprises the variable region.

6. An isolated nucleotide sequence comprising a feline calicivirus C gene having at least one modified consensus splicing site so that the splicing site is inactive when said nucleotide sequence is cloned into a vector that is transcribed in a nucleus.

7. The isolated nucleotide sequence of claim 6, wherein said nucleotide sequence is capable of being transcribed in the nucleus of eukaryotic cells without being altered by splicing machinery found in the eukaryotic cells.

8. An expression vector comprising the nucleotide sequence of claim 6.

9. The expression vector of claim 8, comprising a live feline herpesvirus-1 (FHV-1) expression vector.

10. A cell culture comprising cells infected with the recombinant vector of claims 8 or 9.

11. The cell culture of claim 10, wherein the cells comprise Crandell-Rees Feline Kidney (CRFK) cells.

12. The cell culture according to claim 10, wherein the cells comprise Crandell-Rees Feline Kidney (CRFK) cells.

13. A composition to elicit an immune response comprising the expression vector of claim 8.

14. A composition to elicit an immune response comprising the expression vector of claim 8.

15. A composition to elicit an immune response to feline calicivirus (FCV), comprising the expression vector of claim 8.

16. A composition to elicit an immune response to feline calicivirus (FCV), comprising the expression vector of claim 8.

17. The isolated nucleotide sequence according to claim 6, wherein the consensus splicing site is mutated.

18. An expression vector comprising the nucleotide sequence of claim 17.

19. A host cell comprising the expression vector of claim 18.

20. A composition to elicit an immune response to feline calicivirus (FCV), comprising the nucleotide sequence of claim 17.

21. An isolated nucleotide sequence comprising a portion of feline calicivirus capsid protein gene that encodes an antigenic determinant of the capsid protein, the nucleotide sequence having at least one modified consensus splicing site that is inactive when said isolated nucleotide sequence is cloned into a vector and transcribed in a nucleus.

22. A method for recombinantly expressing the nucleotide sequence according to claim 6 or 21, the method comprising:

(a) inserting the nucleotide sequence into an expression vector, and (b) expressing said nucleotide sequence in a host cell.

23. An expression vector comprising the nucleotide sequence of claim 21.

24. A cell culture comprising cells infected with the expression vector of claim 23.

25. A composition to elicit an immune response comprising the expression vector of claim 23.

26. An isolated nucleotide sequence obtained from the feline calicivirus C gene of FCV stain 2280 (ATCC designation VR-2555) wherein the D1, which represents nucleotide residues 1–6 of SEQ ID NO:24, D2, which represents nucleotide residues 8–13 of SEQ ID NO:24, D3, which represents nucleotide residues 13–19 of SEQ ID NO:24, D4, which represents nucleotide residues 33–37 of SEQ ID NO:24, and D9, which represents nucleotide residues 361–368 of SEQ ID NO:24, splicing sites have been modified so that splicing sites are inactive.

27. An isolated nucleotide sequence obtained from the feline calicivirus C gene of FCV strain 2280 (ATCC designation VR-2555) wherein the D9, which represents nucleotide residues 361–368 of SEQ ID NO:24, splicing site has been modified so that the splicing sites are inactive when said nucleotide sequence is cloned into a vector that is transcribed in a nucleus.

28. An isolated nucleotide sequence obtained from the feline calicivirus C gene of FCV strain 2280 (ATCC designation VR-2555) wherein the D1, which represents nucleotide residues 1–6 of SEQ ID NO:24, D2, which represents nucleotide residues 8–13 of SEQ ID NO:24, D3, which represents nucleotide residues 13–19 of SEQ ID NO:24, and D4, which represents nucleotide residues 33–37 of SEQ ID NO:24, splicing sites have been modified so that the splicing sites are inactive when said nucleotide sequence is cloned into a vector that is transcribed in a nucleus.

29. An isolated nucleotide sequence obtained from the feline calicivirus C gene of FCV strain 2280 (ATCC designation VR-2555) wherein the D9, which represents nucleotide residues 361–368 of SEQ ID NO:24, splicing site has been detected therefrom and the D4, which represents nucleotide residues 33–37 of SEQ ID NO:24, D5, which represents nucleotide residues 113–121 of SEQ ID NO:24, and A2, which is represented by nucleotide SEQ ID NO:7, splicing sites have been inactivated.

30. An isolated nucleotide sequence obtained from the feline calicivirus C gene of FCV strain 2280 (ATCC designation VR-2555) wherein the D4, which represents nucleotide residues 33–37 of SEQ ID NO:24, D5, which represents nucleotide residues 113–121 of SEQ ID NO:24, and A2, which is represented by nucleotide SEQ ID NO:7, splicing sites have been inactivated when said nucleotide sequence is cloned into a vector that is transcribed in a nucleus.

31. An isolated nucleotide sequence obtained from the feline calicivirus C gene of FCV strain 2280 (ATCC designation VR-2555) wherein the D9, which represents nucleotide residues 361–368 of SEQ ID NO:24, splicing site has been deleted therefrom and the D2, which represents nucleotide residues 8–13 of SEQ ID NO:24, D3, which represents nucleotide residues 13–19 of SEQ ID NO:24, D4, which represents nucleotide residues 33–37 of SEQ ID NO:24, D5, which represents nucleotide residues 113–121 of SEQ ID NO:24, and A2, which is represented by nucleotide SEQ ID NO:7, splicing sites have been inactivated.

32. An isolated nucleotide sequence obtained from the feline calicivirus C gene of FCV strain 2280 (ATCC designation VR-2555) wherein the D2, which represents nucleotide residues 8–13 of SEQ ID NO:24, D3, which represents nucleotide residues 13–19 of SEQ ID NO:24, D4, which represents nucleotide residues 33–37 of SEQ ID NO:24, D5, which represents nucleotide residues 113–121 of SEQ ID NO:24, and A2, which is represented by the nucleotide of SEQ ID NO:7, splicing sites have been inactivated when said nucleotide sequence is cloned into a vector that is transcribed in a nucleus.

33. An isolated nucleotide sequence obtained from the feline calicivirus C gene of FCV strain 2280 (ATCC designation VR-2555) wherein the D1, which represents nucleotide residues 1–6 of SEQ ID NO:24, D2, which represents nucleotide residues 8–13 of SEQ ID NO:24, D3, which represents nucleotide residues 13–19 of SEQ ID NO:24, D4, which represents nucleotide residues 33–37 of SEQ ID NO:24, and D9, which represents nucleotide residues 361–368 of SEQ ID NO:24, splicing sites have been deleted therefrom and the D5, which represents nucleotide residues 113–121 of SEQ ID NO:24, and A2, which is represented by nucleotide SEQ ID NO:7, splicing sites have been inactivated.

34. An isolated recombinant DNA molecule wherein a nucleotide sequence comprising a feline calicivirus C gene having at least one modified consensus splicing site so that the splicing site is inactive, is fused to a DNA sequence coding for a polypeptide.

35. An isolated recombinant DNA molecule wherein a nucleotide sequence selected from (a) an isolated nucleotide sequence obtained from the feline calicivirus C gene of FCV strain 2280 (ATCC designation VR-2555) wherein the
D1, which represents nucleotide residues 1–6 of SEQ ID NO:24,
D2, which represents nucleotide residues 8–13 of SEQ ID NO:24,
D3, which represents nucleotide residues 13–19 of SEQ ID NO:24,
D4, which represents nucleotide residues 33–37 of SEQ ID NO:24, and
D9, which represents nucleotide residues 361–368 of SEQ ID NO:24, splicing sites have been modified so that the splicing sites are inactive when said nucleotide sequence is cloned into a vector that is transcribed in a nucleus;

(b) an isolated nucleotide sequence obtained from the feline calicivirus C gene of FCV strain 2280 (ATCC designation VR-2555) wherein the D9, which represents nucleotide residues 361–368 of SEQ ID NO:24, splicing site has been modified so that the splicing site is inactive when said nucleotide sequence is cloned into a vector that is transcribed in the nucleus;

(c) an isolated nucleotide sequence obtained from the feline calicivirus C gene of FCV strain 2280 (ATCC designation VR-2555) wherein the
D1, which represents nucleotide residues 1–6 of SEQ ID NO:24,
D2, which represents nucleotide residues 8–13 of SEQ ID NO:24,
D3, which represents nucleotide residues 13–19 of SEQ ID NO:24, and
D4, which represents nucleotide residues 33–37 of SEQ ID NO:24, splicing sites have been modified so that the splicing sites are inactive when said nucleotide sequence is cloned into a vector that is transcribed in the nucleus;

(d) an isolated nucleotide sequence obtained from the feline calicivirus C gene of FCV strain 2280 (ATCC designation VR-2555) wherein the
(1) D9, which represents nucleotide residues 361–368 of SEQ ID NO:24, splicing site has been deleted therefrom and
(2) the D4, which represents nucleotide residues 33–37 of SEQ ID NO:24, D5, which represents nucleotide residues 113–121 of SEQ ID NO:24, and A2, which is represented by nucleotide SEQ ID NO:7, splicing sites have been inactivated when said nucleotide sequence is cloned into a vector that is transcribed in the nucleus;

(e) an isolated nucleotide sequence obtained from the feline calicivirus C gene of FCV strain 2280 (ATCC designation VR-2555) wherein the
D4, which represents nucleotide residues 33–37 of SEQ ID NO:24,
D5, which represents nucleotide residues 113–121 of SEQ ID NO:24, and
A2, which is represented by nucleotide SEQ ID NO:7, splicing sites have been inactivated when said nucleotide sequence is cloned into a vector that is transcribed in the nucleus;

(f) an isolated nucleotide sequence obtained from the feline calicivirus C gene of FCV strain 2280 (ATCC designation VR-2555) wherein the
(1) D9, which represents nucleotide residues 361–368 of SEQ ID NO:24, splicing site has been deleted therefrom and
(2) the D2, which represents nucleotide residues 8–13 of SEQ ID NO:24,
D3, which represents nucleotide residues 13–19 of SEQ ID NO:24,
D4, which represents nucleotide residues 33–37 of SEQ ID NO:24,
D5, which represents nucleotide residues 113–121 of SEQ ID NO:24, and
A2, which is represented by nucleotide SEQ ID NO:7, splicing sites have been inactivated when said nucleotide sequence is cloned into a vector that is transcribed in the nucleus;

(g) an isolated nucleotide sequence obtained from the feline calicivirus C gene of FCV strain 2280 (ATCC designation VR-2555) wherein
the D2, which represents nucleotide residues 8–13 of SEQ ID NO:24,
D3, which represents nucleotide residues 13–19 of SEQ ID NO:24,
D4, which represents nucleotide residues 33–37 of SEQ ID NO:24,
D5, which represents nucleotide residues 113–121 of SEQ ID NO:24, and
A2, which is represented by the nucleotide of SEQ ID NO:7, splicing sites have been inactivated when said nucleotide sequence is cloned into a vector that is transcribed in the nucleus; and (h) an isolated nucleotide sequence obtained from the feline calicivirus C gene of FCV strain 2280 (ATCC designation VR-2555) wherein
(1) the D1, which represents nucleotide residues 1–6 of SEQ ID NO:24,
D2, which represents nucleotide residues 8–13 of SEQ ID NO:24,
D3, which represents nucleotide residues 13–19 of SEQ ID NO:24,
D4, which represents nucleotide residues 33–37 of SEQ ID NO:24, and
D9, which represents nucleotide residues 361–368 of SEQ ID NO:24, splicing sites have been deleted therefrom and
(2) the D5, which represents nucleotide residues 113–121 of SEQ ID NO:24, and A2, which is represented by nucleotide SEQ ID NO:7, splicing sites have been inactivated when said nucleotide sequence is cloned into a vector that is transcribed in the nucleus, is fused to a DNA sequence coding for a polypeptide.

36. The isolated recombinant DNA molecule of claim 16 or 35, wherein the polypeptide is the feline calicivirus (FCV) capsid protein of FCV strain 2280 (ATCC designation VR-2555).

37. A cell culture comprising cells infected with the recombinant (FHV-1) vector comprising the recombinant DNA of claim 36.

38. The cell culture according to claim 37, wherein the cells comprise Crandell-Rees Feline Kidney (CRFK) cells.

39. A cell culture comprising cells infected with the recombinant (FHV-1) vector comprising the recombinant DNA of claim 34 or 35.

40. The cell culture according to claim 39, wherein the cells comprise Crandell-Rees Feline Kidney (CRFK) cells.

41. A method for obtaining an isolated nucleotide sequence comprising a portion of feline calicivirus capsid protein gene that encodes an antigenic determinant of the capsid protein, the isolated nucleotide sequence having at least one modified consensus splicing site that is inactive when said isolated nucleotide sequence is cloned into a vector and transcribed in a nucleus, the method comprising:

modifying a consensus splicing site of a gene encoding feline calicivirus (FCV) capsid protein so that said consensus splicing site is inactive when said nucleotide sequence is cloned into a vector and transcribed in the nucleus.

42. An isolated recombinant DNA molecule comprising a portion of feline calicivirus capsid protein gene that encodes an antigenic determinant of the capsid protein, the portion having at least one modified consensus splicing site so that splicing site is inactive when said portion is cloned into a vector and transcribed in a nucleus.

43. A method for making an immunogenic composition, the method comprising:

(a) transforming a host cell with an isolated nucleotide sequence comprising a feline calicivirus C gene having at least one modified consensus splicing site that is inactive when said isolated nucleotide sequence is cloned into a vector and transcribed in a nucleus;

(b) expressing a polypeptide from said isolated nucleotide sequence in step (a);

(c) collecting the polypeptide; and (d) mixing the polypeptide with a pharmaceutically acceptable carrier.

44. A method for making an immunogenic composition, the method comprising:

(a) transforming a host cell with an isolated nucleotide sequence comprising a portion of feline calicivirus capsid protein gene that encodes an antigenic determinant of the capsid protein, the nucleotide sequence having at least one modified consensus splicing site that is inactive when said isolated nucleotide sequence is cloned into a vector and transcribed in a nucleus;

(b) expressing a polypeptide from said nucleotide sequence in step (a);

(c) collecting the polypeptide; and (d) mixing the polypeptide with a pharmaceutically acceptable carrier.

45. The method of claim 1, wherein the consensus splicing site is deleted.

* * * * *

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

-continued

```
GATGTGTTCG AAGTTTGAGC ATG                                        23


(2) INFORMATION FOR SEQ ID NO:2:

     (i) SEQUENCE CHARACTERISTICS:
          (A) LENGTH: 39 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:2:

GTGTTCGTGA CAGTATCAAT CAAGCCCAAA ATTGAATTC                       39


(2) INFORMATION FOR SEQ ID NO:3:

     (i) SEQUENCE CHARACTERISTICS:
          (A) LENGTH: 61 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:3:

CGCGGATCCG TCGACCGCAT GCGTGTTCGT GACAGTATCA ATCAAGCCCA AAATTGAATT 60

C                                                                61


(2) INFORMATION FOR SEQ ID NO:4:

     (i) SEQUENCE CHARACTERISTICS:
          (A) LENGTH: 29 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:4:

GGGAAAAGAG TTGACTCTGA GTGGGAGGC                                  29


(2) INFORMATION FOR SEQ ID NO:5:

     (i) SEQUENCE CHARACTERISTICS:
          (A) LENGTH: 28 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:5:

CACCAGAGCC AGAAATAGAG AACCTAAC                                   28


(2) INFORMATION FOR SEQ ID NO:6:

     (i) SEQUENCE CHARACTERISTICS:
          (A) LENGTH: 13 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:6:

CCCGGTATTC CAG                                                   13
```

-continued (2) INFORMATION FOR SEQ ID NO:7:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

CTTACCCCTG CAGG 14

(2) INFORMATION FOR SEQ ID NO:8:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:8:

TTTTATCACC ACAG 14

(2) INFORMATION FOR SEQ ID NO:9:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

TTGTTGTGTA CCAGG 15

(2) INFORMATION FOR SEQ ID NO:10:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

GGGCGAATTT CGAGCTCGGT ACCAGATCTC TCGAAGTTCC AACATGTGCT CAACCTGCGC 60

(2) INFORMATION FOR SEQ ID NO:11:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

CTATGGCTGG GACCCCCACT TTAG 24

(2) INFORMATION FOR SEQ ID NO:12:

(i) SEQUENCE CHARACTERISTICS:

-continued (A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GTGGGACTGT GACCAGTCTC CACTAC 26

(2) INFORMATION FOR SEQ ID NO:13:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

CTGTCACGAA CACGGATCCA AGCTTTTGTT CCC 33

(2) INFORMATION FOR SEQ ID NO:14:

(i) SEQUENCE CHARACTERISTICS:
(A) LENGTH: 37 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

TTGGGATAGG TGTTCACCAT GGCAACTGAC TACATTG 37

(2) INFORMATION FOR SEQ ID NO:15:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

CATTGCCCAC GTGGACGTCA TTCCAGCTAG CATCCTGGTA CA 42

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:16:

CACCAGATCT CACCATGGCT AGCGCCGTCG TTTTACAACG 40

(2) INFORMATION FOR SEQ ID NO:17:

(i) SEQUENCE CHARACTERISTICS:
(A) LENGTH: 39 base pairs
(B) TYPE: nucleic acid
(C) STRANDEDNESS: single
(D) TOPOLOGY: linear -continued (ii) MOLECULE TYPE: DNA (genomic)

(xi) SEQUENCE DESCRIPTION: SEQ ID NO:17:

CCACCACGCT CATCGATAAT TTCACCGCCG AAAGGCGCG 39

(2) INFORMATION FOR SEQ ID NO:18:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

CCAATAACTG TTACACACCA TGGTTAGTGA AAGTGG 36

(2) INFORMATION FOR SEQ ID NO:19:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:19:

GTGTAACCAA GAAGGACGTC ATTCCAGCTT GCAAGGGTGA CATCGG 46

(2) INFORMATION FOR SEQ ID NO:20:

(i) SEQUENCE CHARACTERISTICS:
(A) LENGTH: 63 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:20:

CAATGTAGTC AGTTGCTACG CCGATCCCAA GCTTTGACCC TCCGCTCTCA CTAACTGTAA 60

CAG 63

(2) INFORMATION FOR SEQ ID NO:21:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:21:

GCTGGTTGTA ATTGCATAGT TGCCCGCCGG TGTTAGCTTT TCAGGAATTG 50

(2) INFORMATION FOR SEQ ID NO:22:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:22:

CCAATAACTG TTACACACCA TGGTTAGTGA GAGCGGAGGG TCAAAGCTTG GG 52

(2) INFORMATION FOR SEQ ID NO:23:

(i) SEQUENCE CHARACTERISTICS:
(A) LENGTH: 2007 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:23:

ATGTGCTCAA CCTGCGCTAA CGTGCTTAAA TACTATGGCT GGGATCCCCA CTTTAGATTA 60

GTTGTCAACC CCAACAAATT CCTTTCTGTT GGCTTTTGTG ATAACCCTCT TATGTGTTGC 120

TATCCAGACT TGCTTCCTGA ATTTGGAACC CTGTGGGACT GTGACCAGTC TCCACTACAA 180

ATTTATTTGG AATCTATTCT TGGAGATGAT GAATGGGCTT CTACCTATGA GGCCATTGAT 240

CCCAGCGTAC CCCCAATGCA CTGGGATGCT ATGGGTAAGA TTTTCCAACC ACACCCTGGC 300

GTTCTGATGC ACCATATCAT TGGTGAAGTC GCCAAGGCTT GGGACCCAAA CCTACCACTG 360

TTTTGCTTAG AGGCTGATGA TGGTTCTATC ACGGCCCCTG AGCAAGGAAC GGTTGTTGGT 420

GGGGTCATTG CCGAGCCTAG TGCACAAATG TCAACAGCTG CTGATATGGC CACAGGGAAA 480

AGCGTTGACT CTGAGTGGGA GGCATTCTTT TCCTTCCACA CCAGCGTCAA CTGGAGTACC 540

ACAGAAACTC AAGGAAAGAT TTTATTCAAA CAATCTTTGG GACCCCTCCT AAACCCATAC 600

CTTGAACATC TTGCTAAGCT GTATGTTGCT TGGTCTGGAT CTATTGATGT TAGGTTCTCT 660

ATCTCTGGTT CTGGAGTATA TGGGGGAAAA CTTGCTGCCA TTGTCGTACC ACCTGGTGTA 720

GACCCCGTTC AAAGTACATC AATGCTGCAA TACCCTCATG TTCTCTTTGA CGCTCGTCAA 780

GTGGAACCAG TTATCTTCTC TATTCCTGAT TTAAGGAGTA CTCTCTATCA CCTTATATCT 840

GATACTGATA CTACTTCCCT TGTGATTATG GTGTATAATG ATCTCATTAA CCCTTATGCT 900

AGTGATACAA ACTCTTCTGG ATGCATCGTT ACAGTTGAAA CCAAGCCGGG GCCAGATTTC 960

AAGTTCCACC TTCTAAAACC ACCTGGATCA ATGCTGACAC ACGGTTCAAT ACCTGCTGAC 1020

CTCATCCCAA AGTCGTCCTC CCTTTGGATT GGCAATCGCT ATTGGTCTGA TATCACTGAA 1080

TTTCTTGTCC GTCCCTTTGT CTTCCAAGCA AACCGACACT TTGATTTTAA TCAGGAAACT 1140

GCTGGGTGGA GCACGCCGAG ATTCCGGCCA ATAACTGTTA CAGTTAGTGA AAGTGGTGGG 1200

TCAAAGCTTG GGATAGGTGT TGCAACTGAC TACATTGTTC CCGGTATTCC AGATGGCTGG 1260

CCAGACACAA CAATTCCTGA AAAGCTTACC CCTGCAGGTA ATTATGCAAT TACAACCAGC 1320

AATAACAGTG ACATTGCTAC GGCTACTGAA TACGACCATG CTGATGAAAT CAAAAACAAC 1380

ACAAACTTTA AAAGTATGTA CATCTGTGGA TCATTGCAAA GAGCTTGGGG TGACAAGAAG 1440

ATATCTAATA CTGCTTTTAT CACCACAGCA GTCAAGGAAG GTAACAGCAT CACACCGTCT 1500

AACACAATTG ACATGACTAA GCTTGTTGTG TACCAGGATG CTCACGTGGG CAATGATGTG 1560

CAAACTTCCG ATGTCACCCT TGCACTTCTT GGTTACACAG GAATTGGTGA ACAAGCAATT 1620

GGTTCAGATA GAGATAGAGT GGTGCGAATC AGTGTCCTAC CAGAAACTGG TGCCCGTGGC 1680

GGCAACCACC CCATCTTCTA CAAAAATACA ATTAAATTGG GCTATGTGAT TAGGTCTATT 1740

GATGTGTTTA ACTCCCAGAT CCTCCACACG TCCAGACAAC TATCCCTAAA TCACTACCTG 1800

CTTCCACCTG ATTCCTTTGC TGTCTATAGA ATAATTGATT CTAATGGTTC ATGGTTTGAC 1860

-continued

```
ATTGGTATTG ATAGTGATGG TTTCTCTTTT GTTGGTGTTT CTAGTTTACC CACACTGGAA   1920

TTTCCTCTCT CTGCCTCCTA CATGGGAATT CAATTGGCAA AAATCAGGCT TGCCTCAAAT   1980

ATTAGGAGTA GTATGACAAA ATTATGA                                        2007


(2) INFORMATION FOR SEQ ID NO:24:

     (i) SEQUENCE CHARACTERISTICS:
          (A) LENGTH: 402 base pairs
          (B) TYPE: nucleic acid
          (C) STRANDEDNESS: single
          (D) TOPOLOGY: linear

    (ii) MOLECULE TYPE: DNA (genomic)

    (xi) SEQUENCE DESCRIPTION: SEQ ID NO:24:

GTTAGTGAAA GTGGTGGGTC AAAGCTTGGG ATAGGTGTTG CAACTGACTA CATTGTTCCC     60

GGTATTCCAG ATGGCTGGCC AGACACAACA ATTCCTGAAA AGCTTACCCC TGCAGGTAAT    120

TATGCAATTA CAACCAGCAA TAACAGTGAC ATTGCTACGG CTACTGAATA CGACCATGCT    180

GATGAAATCA AAAACAACAC AAACTTTAAA AGTATGTACA TCTGTGGATC ATTGCAAAGA    240

GCTTGGGGTG ACAAGAAGAT ATCTAATACT GCTTTTATCA CCACAGCAGT CAAGGAAGGT    300

AACAGCATCA CACCGTCTAA CACAATTGAC ATGACTAAGC TTGTTGTGTA CCAGGATGCT    360

CACGTGGGCA ATGATGTGCA AACTTCCGAT GTCACCCTTG CA                       402
```